United States Patent
Yin et al.

(10) Patent No.: US 8,278,282 B2
(45) Date of Patent: Oct. 2, 2012

(54) NUCLEOSIDE ANALOGS FOR TREATMENT OF VIRAL INFECTIONS

(75) Inventors: Zheng Yin, Singapore (SG); Jeyaraj Duraiswamy, Singapore (SG); Yen Liang Chen, Singapore (SG)

(73) Assignee: Novartis AG, Basel (CH)

( * ) Notice: Subject to any disclaimer, the term of this patent is extended or adjusted under 35 U.S.C. 154(b) by 194 days.

(21) Appl. No.: 12/526,079

(22) PCT Filed: Feb. 7, 2008

(86) PCT No.: PCT/EP2008/051527
§ 371 (c)(1),
(2), (4) Date: Oct. 9, 2009

(87) PCT Pub. No.: WO2008/095993
PCT Pub. Date: Aug. 14, 2008

(65) Prior Publication Data
US 2010/0227833 A1    Sep. 9, 2010

(30) Foreign Application Priority Data

Feb. 9, 2007  (EP) .................................... 07102027
Jan. 2, 2008  (EP) .................................... 08150003

(51) Int. Cl.
*A01N 43/04* (2006.01)
*A61K 31/70* (2006.01)

(52) U.S. Cl. ........ 514/42; 514/43; 536/27.1; 536/27.13; 536/27.2

(58) Field of Classification Search ........................ None
See application file for complete search history.

(56) References Cited

U.S. PATENT DOCUMENTS

| 2004/0259934 A1 | 12/2004 | Olsen et al. |
| 2004/0259941 A1 | 12/2004 | May |

FOREIGN PATENT DOCUMENTS

| WO | WO 03/068244 A |   | 8/2003 |
| WO | WO 03/093290 A |   | 11/2003 |
| WO | WO2004/028481  | * | 4/2004 |
| WO | WO 2004/028481 A |   | 4/2004 |

OTHER PUBLICATIONS

International Search Report issued Jul. 23, 2008 for PCT/EP2008/051527 (WO 2008/095993).
Unpublished U.S. Appl. No. 12/536,615, filed Aug. 6, 2009.

* cited by examiner

*Primary Examiner* — Traviss C McIntosh, III
(74) *Attorney, Agent, or Firm* — Banner & Witcoff, Ltd.

(57) ABSTRACT

This invention relates to novel compounds that have various medicinal applications, e.g. for the treatment and/or prevention of viral infections.

8 Claims, No Drawings

NUCLEOSIDE ANALOGS FOR TREATMENT OF VIRAL INFECTIONS

TECHNICAL FIELD

This invention is directed to novel compounds which are useful in the treatment of viral infections. The invention is also directed to pharmaceutical compositions containing the compounds, processes for their preparation and uses of the compounds in various medicinal applications, such as the treatment or prevention of viral infections, particularly dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, more particularly dengue virus and Hepatitis C virus.

BACKGROUND

Dengue fever is a febrile disease caused by one of the four dengue virus serotypes DEN-1, DEN-2, DEN-3 and DEN-4, which belong to the family Flaviviridae. The virus is transmitted to humans primarily by *Aedes aegypti*, a mosquito that feeds on humans.

Infections produce a range of clinical manifestations, from milder flu-like symptoms to the more severe and sometimes fatal hemorrhagic disease. Typical symptoms include fever, severe headache, muscle and joint pains and rashes. The more severe forms of the disease are dengue hemorrhagic fever (DHF) and dengue shock syndrome (DSS). According to the WHO, there are four major clinical manifestations of DHF: (1) high fever (2) haemorrhagic phenomena (3) thrombocytopaenia and (4) leakage of plasma. DSS is defined as DHF plus weak rapid pulse, and narrow pulse pressure or hypotension with cold, clammy skin and restlessness. The severity of DHF can be reduced with early detection and intervention, but patients in shock are at high risk of death.

Dengue is endemic in tropical regions, particularly in Asia, Africa and Latin America, and an estimated 2.5 billion people live in areas where they are at risk of infection. There are around 40 million cases of dengue fever and several hundred thousand cases of DHF each year. In Singapore, an epidemic in 2005 resulted in more than 12000 cases of dengue fever.

Despite regular outbreaks, previously infected people remain susceptible to infection because there are four different serotypes of the dengue virus and infection with one of these serotypes provides immunity to only that serotype. It is believed that DHF is more likely to occur in patients who have secondary dengue infections. Efficient treatments for dengue fever, DHF and DSS are being sought.

Yellow fever virus (YFV), West Nile virus (WNV), Japanese encephalitis virus (JEV), tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus (HCV) also belong to the family Flaviviridae.

WNV can be asymptomatic, or it can cause flu-like symptoms in some individuals. In some cases it causes neurological disorders, encephalitis, and in severe cases can result in death. WNV is also transmitted by mosquitos. YFV is another mosquito-borne virus, which can cause severe symptoms in infected individuals. JEV is also transmitted by mosquitoes, and is either asymptomatic or causes flu-like symptoms, with some cases developing into encephalitis. The acute encephalitis stage of the disease is characterised by convulsions, neck stiffness and other symptoms.

HCV is a blood-borne virus that is transmitted by blood-to-blood contact. In the initial (acute) stage of the disease, most patients will not show any symptoms. Even during the chronic stage (i.e. where the disease persists for more than 6 months), severity of symptoms can vary from patient to patient. In the long term, some infected persons can progress to cirrhosis and liver cancer. The current treatment for HCV involves a combination of interferon alpha and ribavirin, an anti-viral drug.

Efficient treatments for infections caused by these Flaviviridae viruses are being sought as well.

It has now surprisingly been found that certain nucleoside analogs are useful for the treatment of viral infections such as those caused by a virus of the family Flaviviridae, especially dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein.

It is an object of the invention to provide novel compounds. It is also an object of the invention to provide uses of such compounds, for example, for the treatment of viral infections.

DISCLOSURE OF THE INVENTION

The invention provides compounds and pharmaceutical compositions thereof, which are useful for the treatment of viral infections.

In a first aspect, the invention provides a compound of formula (I), or a pharmaceutically acceptable salt or prodrug thereof:

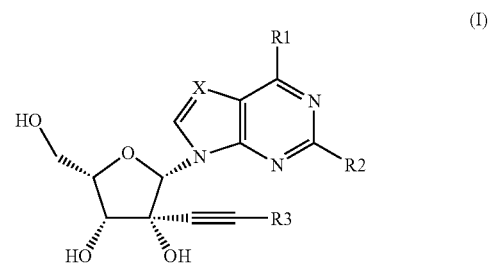

wherein:
X is CH or CR4;
R1 is halogen, NR5R6 or OR7;
R2 is H, halogen, or NR5R6;
R3 is H, alkyl, alkenyl, alkynyl, aryl, cycloalkyl, heterocycloalkyl or heteroaryl, each of which is optionally substituted with one or more substituents;
R4 is alkyl, alkenyl, alkynyl, aryl, cycloalkyl, heterocycloalkyl, heteroaryl, halogen, cyano, nitro, hydroxy, alkoxy, alkylthio, amino, alkylamino, carboxy, carboxamide or alkyloxycarbonyl, each of which is optionally substituted with one or more substituents;
R5 and R6 are independently selected from the group consisting of H, alkyl, alkenyl, alkynyl, aryl, cycloalkyl, heterocycloalkyl, heteroaryl, amino, alkylamino, arylamino, hydroxy, alkoxy, arylcarbonyl and alkylcarbonyl, each of which is optionally substituted with one or more substituents; and
R7 is H, alkyl, alkenyl, alkynyl, aryl, cycloalkyl, heterocycloalkyl, heteroaryl, alkylcarbonyl or arylcarbonyl, each of which is optionally substituted with one or more substituents.

In second aspect, the invention provides a compound of formula (II) or a pharmaceutically acceptable salt or prodrug thereof:

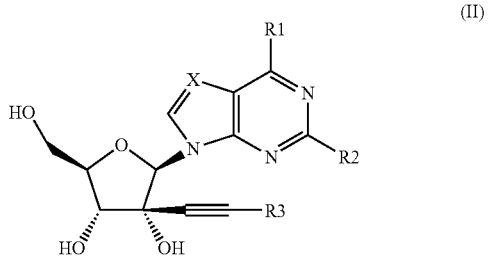

wherein:
X is CH or CR4;
R1 is halogen, NR5R6 or OR7;
R2 is H, halogen, or NR5R6;
R3 is H, alkyl, alkenyl, alkynyl, aryl, cycloalkyl, heterocycloalkyl or heteroaryl, each of which is optionally substituted with one or more substituents;
R4 is alkyl, alkenyl, alkynyl, aryl, cycloalkyl, heterocycloalkyl, heteroaryl, halogen, cyano, nitro, hydroxy, alkoxy, alkylthio, amino, alkylamino, carboxy, carboxamide or alkyloxycarbonyl, each of which is optionally substituted with one or more substituents;
R5 and R6 are independently selected from the group consisting of H, alkyl, alkenyl, alkynyl, aryl, cycloalkyl, heterocycloalkyl, heteroaryl, amino, alkylamino, arylamino, hydroxy, alkoxy, arylcarbonyl and alkylcarbonyl, each of which is optionally substituted with one or more substituents; and
R7 is H, alkyl, alkenyl, alkynyl, aryl, cycloalkyl, heterocycloalkyl, heteroaryl, alkylcarbonyl or arylcarbonyl, each of which is optionally substituted with one or more substituents.

In some examples of the above formulae (I) and (II) X is CH. In other examples, X is CR4.

In the above formulae (I) and (II), R3 may be, for example, H, alkyl, cycloalkyl, aryl, alkenyl or alkynyl. In some examples, R3 is H, lower alkyl, lower alkenyl or lower alkynyl, In some examples R3 is H, lower alkyl or lower alkynyl. In some examples R3 is H or ethynyl.

In the above formulae (I) and (II), R4 may be, for example, halogen, alkyl, cycloalkyl, aryl, alkenyl or alkynyl. In some examples, R4 is halogen, lower alkyl, lower alkenyl or lower alkynyl. In some examples R4 is F, I, or lower alkynyl, e.g. ethynyl.

In the above formulae (I) and (II), R2 may be, for example, H or NR5R6, where R5 and R6 are independently selected from the group consisting of H, alkyl, alkenyl and alkynyl. In some examples R2 is H. In other examples, R2 is NH$_2$. In other examples R2 is halogen. In other examples, one of R5 and R6 is H and the other is selected from the group consisting of alkyl, alkenyl and alkynyl.

In the above formulae (I) and (II), R1 may be, for example, halogen, NR5R6 or OR7 where R7 is selected from the group consisting of H, alkyl, alkenyl and alkynyl. In some examples R7 is lower alkyl, e.g. methyl, ethyl, propyl or butyl. In some examples R7 is methyl. In some examples, R5 and R6 are each independently selected from alkyl, alkenyl and alkynyl. In some examples R1 is halogen, NR5R6 or OR7 where R7 is H or alkyl; R5 and R6 are each independently selected from the group consisting of H and alkyl; R3 is H or lower alkynyl and R4 is halogen or lower alkynyl.

Where R1 is halogen it may be, for example, Cl or Br. In some examples R1 is Cl. Where R1 is OR7, R7 may be H or lower alkyl. In some examples R7 is methyl. Where R1 is NR5R6, it may be, for example, NH$_2$ or NHR5 where R5 is lower alkyl, such as methyl.

X may be, for example, CH and R1 may be NH$_2$ or Cl. In one embodiment X is CH, R1 is NH$_2$ or Cl, and R2 is H.

X may be, for example, CR4 and R1 may be NH$_2$. In one embodiment X is CR4 and R1 is NH$_2$, where R4 is alkynyl, e.g. lower alkynyl, e.g. ethynyl.

Any alkyl or cycloalkyl group in the compound of formula (I) or (II) as defined above may be substituted with one or more substituents selected from the group consisting of halogen, hydroxy, amino, alkylamino, dialkylamino, alkylcarbonyl, arylcarbonyl, cyano, nitro and azido.

Any alkenyl or alkynyl group in the compound of formula (I) or (II) as defined above may be substituted with one or more substituents selected from the group consisting of halogen, hydroxy, amino, alkylamino, dialkylamino, alkylcarbonyl, arylcarbonyl, cyano, nitro and azido.

Any aryl, heteroaryl or heterocyclo group in the compound of formula (I) or (II) as defined above may be substituted with one or more substituents selected from the group consisting of halogen, hydroxy, amino, alkylamino, dialkylamino, alkylcarbonyl, arylcarbonyl, cyano, nitro and azido.

In some examples, any alkyl, alkenyl or alkynyl group in the compound of formula (I) or (II) is a lower alkyl, alkenyl or alkynyl group. In some examples, any aryl group in the compound of formula (I) or (II) above is phenyl.

One group of compounds of comprises substantially pure optically active isomers wherein the stereochemistry of the tetrahydrofuranyl group with regard to the substituents on all asymmetric carbon centres (i.e. the four carbons of the tetrahydrofuranyl ring) is identical to that of Example 1.

One group of compounds comprises substantially pure optically active isomers wherein the stereochemistry of the tetrahydrofuranyl group with regard to the substituents on all asymmetric carbon centres (i.e. the four carbons of the tetrahydrofuranyl ring) is opposite to that of Example 1.

In one embodiment, the invention provides a compound selected from the group consisting of:

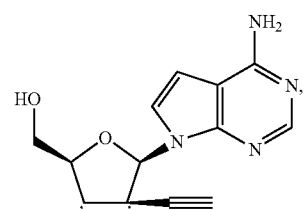

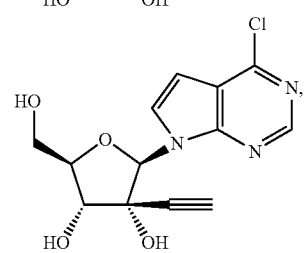

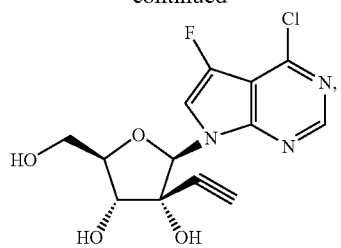
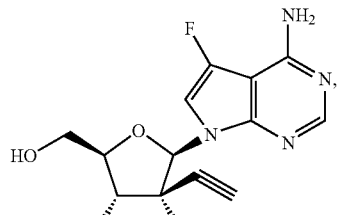
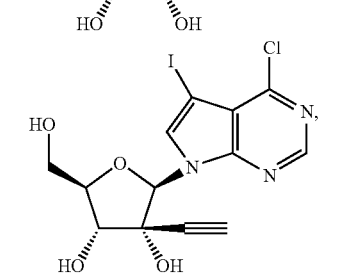
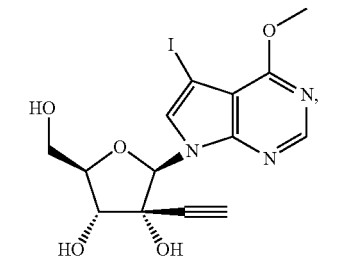
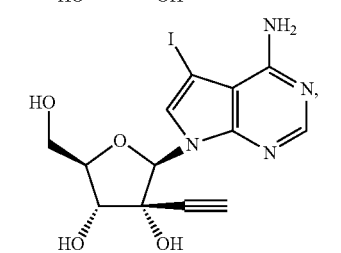
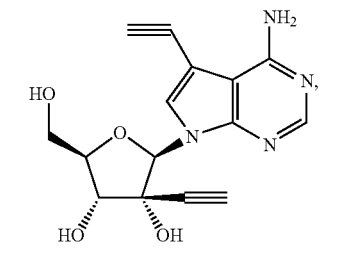
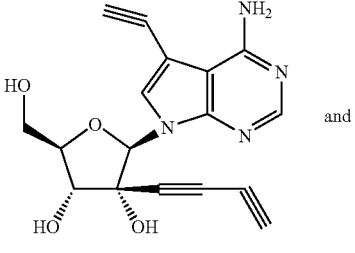

and

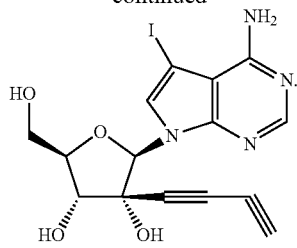

In another embodiment, the invention provides (2R,3R,4R,5R)-2-(4-amino-pyrrolo[2,3-d]pyrimidin-7-yl)-3-ethynyl-5-hydroxymethyl-tetrahydrofuran-3,4-diol.

In another embodiment, the invention provides (2R,3R,4R,5R)-2-(4-amino-5-ethynyl-pyrrolo[2,3-d]pyrimidin-7-yl)-3-ethynyl-5-hydroxymethyl-tetrahydrofuran-3,4-diol.

In another embodiment, the invention provides (2R,3R,4R,5R)-2-(4-amino-5-fluoro-pyrrolo[2,3-d]pyrimidin-7-yl)-3-ethynyl-5-hydroxymethyl-tetrahydrofuran-3,4-diol.

In another aspect the invention provides a pharmaceutical composition comprising a compound of formula (I) or (II) as defined above, in association with at least one pharmaceutically acceptable excipient, e.g. appropriate diluent and/or carrier, e.g. including fillers, binders, disintegrators, flow conditioners, lubricants, sugars or sweeteners, fragrances, preservatives, stabilizers, wetting agents and/or emulsifiers, solubilisers, salts for regulating osmotic pressure and/or buffers.

In another aspect, the invention provides a compound of formula (I) or (II) as defined above for use as a medicament.

In another aspect the invention provides a compound of formula (I) or (II) for the manufacture of a medicament.

In another aspect the invention provides the use of a compound of formula (I) or (II) for the manufacture of a medicament, e.g. a pharmaceutical composition, for the treatment and/or prevention of a viral infection.

In another aspect the invention provides the use of a compound of formula (I) or (II) as a pharmaceutical, e.g. for the treatment and/or prevention of a viral infection.

In another aspect, the invention provides a compound of formula (I) or (II) as defined above for use in the treatment and/or prevention of a viral infection.

In another aspect, the invention provides the use of a compound of formula (I) or (II) as defined above in the manufacture of a medicament for the treatment and/or prevention of a disease caused by a viral infection.

In still another aspect, the invention provides a method of treating and/or preventing a disease caused by a viral infection, comprising administering to a patient in need thereof an effective amount of a compound of formula (I) or (II) as defined above.

In yet another aspect, the invention provides a pharmaceutical composition for the treatment and/or prevention of a disease caused by a viral infection, comprising a compound of formula (I) or (II) as defined above.

The viral infection is, for example, caused by a virus of the family Flaviviridae, such as dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus, Gadgets Gully virus, Kyasanur Forest disease virus, Langat virus, Louping ill virus, Powassan virus, Royal Farm virus, Karshi virus, Kadam virus, Meaban virus, Saumarez Reef virus, Tyuleniy virus, Aroa virus, Bussuquara virus, Iguape virus, Naranjal virus, Kedougou virus, Cacipacore virus, Koutango virus, Alfuy virus, Usutu virus, Yaounde virus, Kokobera virus, Stratford virus, Bagaza virus, Ilheus virus, Rocio virus, Israeli turkey meningoencephalomyelitis virus, Ntaya virus, Tembusu virus, Sponweni virus, Banzi virus, Bouboui virus, Edge Hill virus, Jugra virus, Potiskum virus, Saboya virus, Sepik virus, Uganda virus, Wesselsbron virus, Entebbe bat virus, Sokoluk virus, Yokose virus, Apoi virus, Cowbone Ridge virus, Jutiapa virus, modoc virus, Sal Vieja virus, San Perlita virus, Bukalasa bat virus, Carey Island virus, Dakar bat virus, Mantana myotis leukoencephalitis virus, Batu Cave virus, Phnom Penh bat virus, Rio Bravo virus, Cell fusing agent virus, Tamana bat virus and Hepatitis C virus, especially dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, particularly dengue virus and Hepatitis C virus.

In another aspect the invention provides a combination of a compound of formula (I) or (II) with at least one second drug substance.

In another aspect the invention provides a pharmaceutical combination, e.g. a kit, comprising a) a first agent which is a compound of formula (I) or (II), in free form or in pharmaceutically acceptable salt form, and b) at least one co-agent. The kit may comprise instructions for its administration.

In the above methods for using the compounds of the invention, a compound of formula (I) or (II) may be administered to a system comprising cells or tissues. In other embodiments, a compound of formula (I) or (II) may be administered to a human or animal patient.

A process for preparing a compound of formula (I) or (II) as defined above, includes the step of coupling a compound of formula (I)

(i)

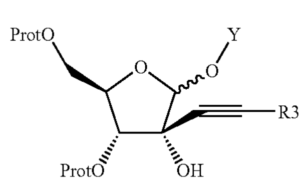

or a corresponding epoxide wherein the group —OY and the adjacent —OH are replaced by —O— with a compound of formula (ii)

(ii)

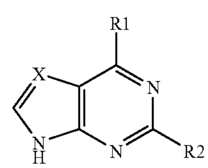

to give a compound of formula (iii)

(iii)

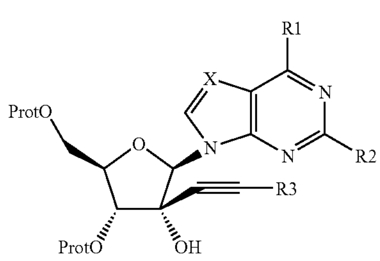

where X, R1, R2 and R3 are as defined above, Y represents H or alkyl, such as lower alkyl, e.g. methyl and Prot represents a protecting group, preferably a benzyl group, optionally substituted with one or more halogens, or a benzoyl group, or a toluoyl group or a silyl group. If desired, compounds of formula (I) may be converted into other compounds of formula (I). Compounds of formula (i) and of formula (ii) are known compounds or may be prepared according to known methods, e.g. analogously to a method as described herein.

Compounds provided by the invention are hereinafter designated as "compound(s) of the invention". A compound of the invention includes a compound in any form, e.g. in free form, in the form of a salt, in the form of a solvate and in the form of a salt and a solvate.

The term "alkyl" as used herein refers to branched or straight chain hydrocarbon groups, comprising preferably 1 to 15 carbon atoms. The same terminology applies to the non-aromatic moiety of an alkylaryl group. Examples of alkyl groups include, but are not limited to, methyl, ethyl, propyl, butyl, pentyl, hexyl, heptyl, nonyl, decyl etc. An alkyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The term "lower alkyl" as used herein refers to branched or straight chain alkyl groups comprising 1 to 6 carbon atoms, preferably 1 to 4 carbon atoms. Examples of lower alkyl groups include, but are not limited to, methyl, ethyl, n-propyl, i-propyl, n-butyl, i-butyl, sec-butyl, t-butyl, pentyl, and hexyl. A lower alkyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The term "cycloalkyl" refers to a saturated or partially saturated (non-aromatic) ring comprising preferably 3 to 8 carbon atoms. Examples include, but are not limited to, cyclopropyl, cyclobutyl, cyclopentyl, cyclohexyl and cycloheptyl. A cycloalkyl group is preferably a 3-, 5- or 6-membered ring. A cycloalkyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The term "alkenyl" as used herein refers to branched or straight chain groups, comprising preferably 2 to 15 carbon atoms, more preferably 2 to 6 carbon atoms, still more preferably 2 or 3 carbon atoms, and containing one or more double bonds. Examples of alkenyl groups include, but are not limited to, ethenyl, propenyl, butenyl, penentyl, hexenyl, heptenyl, nonenyl decenyl etc. An alkenyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The term "alkynyl" as used herein refers to branched or straight chain groups, comprising preferably 2 to 15 carbon atoms, more preferably 2 to 6 carbon atoms still more preferably 2 or 3 carbon atoms, and most preferably 2 carbon atoms, and containing one or more triple bonds. Examples of alkynyl groups include, but are not limited to, ethynyl, propynyl, butynyl, penyntyl, hexynyl, heptynyl, nonynyl decynyl etc. An alkenyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The terms "lower alkenyl" and "lower alkynyl" have corresponding meanings to the term "lower alkyl" as defined above. Examples of lower alkenyl and lower alkynyl groups include, but are not limited to, ethenyl, propenyl, butenyl, ethynyl, propynyl and butynyl. A lower alkenyl or alkynyl group may be unsubstituted or optionally substituted with one or more substituents selected from halogen, hydroxy, amino, alkylamino, dialkylamino, alkylcarbonyl, arylcarbonyl, cyano, nitro and azido. Typically it is unsubstituted.

The term "alkoxy" as used herein refers to —OR where R is alkyl as defined above. The term "lower alkoxy" has a corresponding meaning to the term "lower alkyl" as defined above. Examples of lower alkoxy groups include, but are not limited to, methoxy, ethoxy, n-propoxy, i-propoxy, n-butoxy, i-butoxy, sec-butoxy and t-butoxy. Typical examples of lower alkoxy include methoxy, ethoxy, and t-butoxy.

The term "halo" or "halogen" as used herein refers to F, Cl, Br or I, preferably Br or Cl.

The term "aryl" as used herein refers to an aromatic ring having 6 to 18 carbon atoms and includes monocyclic groups as well as multicyclic groups, e.g. fused groups such as bicyclic and tricyclic groups. Preferred aryl groups are those which contain from 6 to 12 carbon atoms, preferably 6 carbon atoms for monocyclic rings and 9 or 10 carbon atoms for fused bicyclic rings. Examples include, but are not limited to, phenyl group, naphthyl group and anthracenyl group, especially phenyl group. An aryl group may be unsubstituted or substituted at one or more ring positions with one or more substituents selected from halogen, hydroxy, amino, alkylamino, dialkylamino, alkylcarbonyl, arylcarbonyl, cyano, nitro, azido. Typically it is unsubstituted.

The term "heteroaryl" means an aromatic ring having 5 to 18 atoms, preferably 5 or 6 atoms, including at least one heteroatom, such as, but not limited to, N, O and S, within the ring. The term "heteroaryl" includes monocyclic groups as well as multicyclic groups, e.g. fused groups such as bicyclic and tricyclic groups. The heteroaryl may optionally be fused or bridged with one or more benzene rings and/or to a further heteroaryl ring and/or to an alicyclic ring.

The term "heterocyclo", "heterocycloalkyl" or "heterocyclic" means a saturated or partially saturated (non-aromatic) ring having 5 to 18 atoms, preferably 5 or 6 atoms, including at least one heteroatom, such as, but not limited to, N, O and S, within the ring. The heterocycle may optionally be fused or bridged with one or more benzene rings and/or to a further heterocyclic ring and/or to an alicyclic ring.

Examples of heterocyclic and heteroaryl groups include, but are not limited to, morpholinyl, piperazinyl, piperidinyl, pyridyl, pyrrolidinyl, pyrazinyl, pyrimidinyl, purinyl, benzimidazolyl, benzoxazolyl, benzothiazolyl, benzofuranyl, benzofurazanyl, benzopyrazolyl, benzotriazolyl, benzothiophenyl, carbazolyl, carbolinyl, cinnolinyl, indolyl, isoindolyl indolinyl, imidazolyl, indolazinyl, indazolyl, morpholinyl, quinoxalinyl, quinolyl, isoquinolyl, quinazolinyl, 1,2,3,4-tetrahydroquinolinyl, tetrahydropyranyl, tetrazolopyridyl, thiadiazolyl, thienyl, azetidinyl, 1,4-dioxanyl, hexahydroazepinyl, pyridine-2-one, thiomorpholinyl, dihydrobenzimidazolyl, dihydrobenzofuranyl, dihydrobenzothiophenyl, dihydrobenzoxazolyl, didhydrofuranyl, dihydroimidazolyl, dihydroisoxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, thiazolyl, isothiazolyl, isoxazolyl, imidazolyl, indanyl, naphthpyridinyl, oxadiazolyl, oxazolyl, oxazoline, isoxazoline, oxetanyl, pyranyl, pyrazinyl, pyridopyridinyl, pyridazinyl, pyrrolyl, pyrazolyl, pyrrolyl, phenanthridinyl, triazolyl, thienyl, furanyl, isobenzofuranyl, or tetrazolyl, particularly N-containing heterocycles such as pyridyl, piperidinyl, pyrimidinyl, pyrrolidinyl, piperazinyl, isoquinolyl, quinazolinyl, 2,2,6,6-tetramethylpiperidyl and morpholinyl.

The terms "alkylcarbonyl" and "arylcarbonyl" include moieties where the C atom of a carbonyl group is bound to a C atom of an alkyl or aryl moiety.

The term "substituted" is intended to describe moieties having substituents replacing a hydrogen on one or more atoms, e.g. C, O or N, of a molecule.

By the term "one or more substituents" is contemplated up to, for example, 3 substituents, preferably one substituent. Two or more substituents may be independently chosen.

Multicyclic moieties include those with two or more rings, e.g. cycloalkyls, aryl, heteroaryls and heterocyclyls in which two or more carbons are common to two adjoining rings ("fused" rings) or in which the rings are joined through non-adjacent/shared atoms ("bridged" rings).

The term "prodrug" as used herein means a pharmacologically acceptable derivative of the compound of formula (I) or (II), such that an in vivo biotransformation of the derivative gives the compound as defined in formula (I) or (II). Prodrugs of compounds of formula (I) and (II) may be prepared by modifying functional groups present in the compounds, such as hydroxy or acid groups, in such a way that the modified groups are cleaved in vivo to give the parent compound. Suitable prodrugs include, for example, esters or amides.

The term "salts" includes therapeutically active non-toxic acid addition salts derived from the compounds of formula (I) and (II). Acid addition salts can be obtained by treating the base form of the compounds with appropriate acids. Suitable acids include inorganic acids, for example hydrohalic acid, in particular hydrochloric acid, hydrobromic acid, sulfuric acid, nitric acid and phosphoric acid; and organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicyclic acid, pamoic acid, hexanoic acid, cyclopentanepropionic acid, glycolic acid, pyruvic acid, lactic acid, tartaric acid, benzoic acid, 3-(4-hydroxybenzoyl)benzoic acid, cinnamic acid, mandelic acid, 1,2-ethane-disulfonic acid, 2-hydroxyethanesulfonic acid, 4-chlorobenzenesulfonic acid, 2-napthalenesulfonic acid, camphorsulfonic acid, 3-phenylpropionic acid, trimethylacetic acid, t-butylacetic acid, lauryl sulfuric acid, gluconic acid, glutamic acid, hydroxynaphthoic acid and stearic acid.

The term "protecting group" means a group that masks a functional group in a molecule, so that chemoselectivity is possible during a reaction. Suitable protecting groups are preferably simple to incorporate, stable to the relevant reaction conditions and easy to remove. Such protecting groups are known to those skilled in the art and are described in Protective Groups in Organic Synthesis by Theodora W Greene (John Wiley & Sons Canada, Ltd). Suitable protecting groups include, for example, benzyl group, optionally substituted with one or more halogens (e.g. dichlorobenzyl group), or benzoyl group or toluoyl group or silyl group.

The terms "treat", "treating", "treated" or "treatment" include the diminishment or alleviation of at least one symptom associated with or caused by the state, disease or disorder being treated. For example, treatment can include diminishment of one or more of the following: viremia or fever in a patient.

The terms "prevent", "preventing" or "prevention" include the prevention of at least one symptom associated with or caused by the state, disease or disorder being prevented. For example, prevention can include the prevention of one or more of the following: viremia or fever in a patient.

The term "patient" includes organisms that are capable of suffering from, or afflicted or infected with, a viral infection, e.g. mammals such as humans, apes, monkeys, cows, horses, pigs, sheep, cats, dogs, goats, mice, rabbits, rats and transgenic non-human animals. In some embodiments the patient is a human, e.g. a human capable of suffering from, or afflicted with, a disease or condition described herein, e.g. an infection caused by a virus of the family Flaviviridae, e.g. infection caused by dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein.

Dengue virus is intended to include any of the dengue virus serotypes 1, 2, 3 and 4.

A "disease caused by a viral infection" includes disorders and states that are associated with the activity of a virus, e.g. infection with a virus, e.g. infection caused by a virus of the family Flaviviridae, e.g. infection caused by dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein, in a patient.

The "effective amount" of a compound of the invention is the amount necessary or sufficient to treat or prevent a disease caused by a viral infection, e.g. infection caused by a virus of the family Flaviviridae, e.g. infection caused by dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein, e.g. the effective amount is the amount necessary to treat or prevent one or more symptoms of a viral infection. The effective amount can vary depending on the compound employed, the mode of administration, the treatment desired and the disease indicated, as well as other factors such as a patient's age, body weight, general health and sex. For example, the choice of the compound of the invention can affect what constitutes an "effective amount". One of ordinary skill in the art would be able to study the factors described herein and make a determination regarding the effective amount of a compound of the invention without undue experimentation. The regimen of administration can affect what constitutes an effective amount. The compound of the invention can be administered to a patient either prior to or after the onset of a disease caused by a viral infection, e.g. prior to or after infection caused by a virus of the family Flaviviridae. Furthermore, several divided dosages, as well as staggered dosages, can be administered daily or sequentially, or the dose can be continuously infused, or can be a bolus injection. Further, the dosages of the compounds of the invention can be proportionally increased or decreased as indicated by the exigencies of the therapeutic or prophylactic situation. A physician or veterinarian having ordinary skill in the art can readily determine and prescribe the effective amount required. For example, the physician or veterinarian could start doses of the compounds of the invention employed in a pharmaceutical composition at levels lower than that required in order to achieve the desired therapeutic effect and gradually increase the dosage until the desired effect is achieved.

The term "pharmaceutical composition" includes preparations, for example medicaments, suitable for administration to mammals, e.g. humans.

The compounds of the invention containing acidic protons may also be converted into their therapeutically active non-toxic base addition salt forms by treatment with appropriate organic and inorganic bases. Appropriate base salts forms include, for example, ammonium salts, alkaline and alkaline earth metal salts, in particular lithium, sodium, potassium, magnesium and calcium salts, salts with organic bases, e.g. benzathine, N-methyl-D-glucamine and hybramine salts, and salts with amino acids, for example arginine and lysine.

Conveniently, the acid or base addition salt forms can be converted into the free forms by treatment with an appropriate base or acid.

The term addition salt as used in the present context also comprises the solvates which the compounds of the invention, as well as the salts thereof, are able to form. Such solvates include, for example, hydrates and alcoholates.

It will be appreciated that the compounds of the invention may exist in the form of optical isomers, racemates or diastereoisomers. The scope of this invention embraces all stereochemically isomeric forms of the compounds. The term "stereochemically isomeric forms" as used herein therefore means all possible isomeric forms which the compounds of the invention may possess. In particular, asymmetric carbons may have the R- or S-configuration. For example, the asymmetric carbons of the tetrahydrofuranyl moieties of the compounds of the invention may have the R- or S-configuration.

It will also be appreciated that the compounds of the invention can exist as tautomers. For example, compounds of the invention where R1 is OH or $NH_2$ or where R2 is $NH_2$ may exist as tautomeric forms. The scope of this invention embraces all such tautomeric forms.

The compounds of the invention, and particularly as exemplified, in free or pharmaceutically acceptable addition salt form, exhibit pharmacological activity and are useful as pharmaceuticals, particularly for the treatment and/or prevention of viral infections such as those caused by members of the family Flaviviridae. The compounds are particularly useful for the treatment and/or prevention of infections such as those caused by dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein.

The compounds of Examples 1-10 are preferred compounds of the invention. It has, for example been determined that the compounds of the invention, including the compounds of Examples 1-10, exhibit activity in a cell-based flavivirus immuno (CFI) assay, a cell-based flavivirus cytopathic effect (CPE) assay and an HCV replicon assay, and in vivo in a mouse model of dengue virus infection. The tests are carried out as described in the Examples section.

In the CFI assay for dengue virus, the compounds of the invention are indicated to exhibit $EC_{50}$ values that are below 14 μM, preferably below 5 μM, preferably below 3 μM, more preferably below 2 μM, even more preferably below 1 μM, most preferably below 0.8 μM. For example, the $EC_{50}$ value for the compound of Example 1 is about 0.2 μM (e.g. with dengue virus serotype 1 and dengue virus serotype 4), the $EC_{50}$ value for the compound of Example 4 is about 0.4 μM (e.g. with dengue virus serotype 2), the $EC_{50}$ value for the compound of Example 8 is about 0.6 μM (e.g. with dengue virus serotype 2).

In the CFI assay for yellow fever virus, the compounds of the invention are indicated to exhibit $EC_{50}$ values that are below 5 µM, preferably below 3 µM, more preferably below 2 µM, even more preferably below 1.5 µM, most preferably below 0.9 µM. For example, the $EC_{50}$ value for the compound of Example 1 is about 0.9 µM.

In the CPE assay for West Nile virus, the compounds of the invention are indicated to exhibit $EC_{50}$ values that are below 5 µM, preferably below 3 µM, preferably below 2 µM, more preferably below 1.5 µM, most preferably below 1.3 µM. For example, the $EC_{50}$ value for the compound of Example 1 is about 3.75 µM.

In the CPE assay for Japanese encephalitis virus the compounds of the invention are indicated to exhibit $EC_{50}$ values that are below 5 µM, more preferably below 4 µM. For example, the $EC_{50}$ value for the compound of Example 1 is about 1.3 µM In the HCV replicon assay, the compounds of the invention are indicated to exhibit $EC_{50}$ values that are below 5 µM, preferably below 2 µM, more preferably below 1 µM, more preferably below 0.7 µM, even more preferably below 0.5 µM, even more preferably below 0.3 µM, even more preferably below 0.2 µM, most preferably below 0.1 µM. For example, the $EC_{50}$ value for the compound of Example 1 is about 0.1 µM.

The CFI assay is based on quantitative immunodetection of the viral envelope protein, E, as a readout for viral load in target cells. In the CFI assay, the compounds of the invention show activity against dengue virus and Yellow fever virus. Furthermore, the compounds of the invention show activity against Japanese encephalitis virus in a CPE assay. In this assay, the activities of the compounds of the invention are determined by evaluating the inhibition of virus-induced CPE in target cells. The compounds of the invention also exhibit anti-HCV activity in an HCV replicon assay.

It is therefore indicated that for the treatment of viral infections, such as those caused by a virus of the family Flaviviridae, for example dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C virus, and other Flaviviridae viruses as described herein, a compound of the invention may be administered to larger mammals, for example humans, by similar modes of administration at similar dosages to those conventionally used.

Moreover, it will be appreciated that the dosage range of a compound of the invention to be employed for treating and/or preventing a viral infection depends upon factors known to the person skilled in the art, including host, nature and severity of the condition to be treated, the mode of administration and the particular substance to be employed.

The daily dosage of the compound of the invention will vary with the compound employed, the mode of administration, the treatment desired and the disease indicated, as well as other factors such as a patient's age, body weight, general health, condition, prior medical history and sex, and like factors known in the medical arts. For example, a compound of the invention is administered at a daily dosage in the range from about 0.5 mg/kg body weight to about 15 mg/kg body weight, e.g. in the range from about 1 mg/kg body weight to about 10 mg/kg body weight. Typically, satisfactory results can be obtained when the compound of the invention is administered at a daily dosage from about 0.001 g to about 1.5 g, e.g. not exceeding about 1 gram, e.g. from about 0.1 g to about 0.5 g for a 70 kg human, given up to 4 times daily.

For example, an indicated daily dosage for a compound of Example 1 for the treatment of a dengue viral infection is about 200-400 mg, preferably given once daily, for a 70 kg human.

For pharmaceutical use one or more compounds of the invention may be used, e.g. one, or a combination of two or more compounds of the invention, preferably one compound of the invention, is used.

When the compounds of the invention are administered as pharmaceuticals to a patient, e.g. to a mammal, e.g. a human, they can be given per se, or as a pharmaceutical composition. The compounds of the invention may be formulated into various pharmaceutical forms for such administration purposes. Any suitable compositions usually employed for systemically administering drugs may be used. The compounds of the invention may be formulated for administration by any suitable route, for example orally, parenterally, by inhalation spray, transdermally, nasally (e.g. as by a spray), topically (e.g. as by powders, ointments or drops), rectally, vaginally, sublingually, bucally or via an implanted reservoir. In some examples the compounds of the invention are administered orally.

To prepare the pharmaceutical compositions of this invention, an effective amount of a compound of the invention, as active ingredient, optionally in addition salt form, is combined in intimate admixture with a pharmaceutically acceptable carrier. In general, the formulations are prepared by uniformly and intimately bringing into association a compound of the invention with liquid carriers, or finely divided solid carriers, or both, and then, if necessary, shaping the product. The pharmaceutically acceptable carrier includes a pharmaceutically acceptable material, composition or vehicle, suitable for administering compounds of the invention to a patient. Carriers include liquid or solid filler, diluent, excipient, solvent or encapsulating material, involved in carrying or transporting the compound of the invention from one organ or portion of the body to another organ or portion of the body. The carrier may take a wide variety of forms depending on the form of preparation desired for administration. Carriers may be acceptable in the sense of being compatible with the other ingredients of the formulation, and not injurious to the patient. Suitable carriers include, but are not limited to, sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; water, glycols, oils, alcohols and the like in the case of oral liquid preparations; solid carriers such as kaolin; other diluents, lubricants, binders, disintegrating agents and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: water soluble antioxidants, such as ascorbic acid, cysteine hydrochloride, sodium bisulfate, sodium metabisulfite, sodium sulfite and the like;

oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Preferred pharmaceutical compositions include those in unit dosage form suitable for administration orally or by parenteral injection.

For oral administration the compounds can be formulated into solid or liquid preparations such as tablets, capsules, powders, pills, solutions, suspensions, syrups, elixirs, emulsions and dispersions. In preparing these oral dosage forms, any of the usual pharmaceutical media may be employed, such as water, glycols, oils, alcohols and the like in the case of oral liquid preparations or solid carriers such as starches, sugars, kaolin, diluents, lubricants, binders, disintegrating agents and the like. Other components such as colourings, sweeteners or flavourings may be added. Because of their ease of administration, tablets and capsules represent the most advantageous oral dosage unit forms in which case solid pharmaceutical carriers may be employed.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The phrase "parenteral administration" or the like as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Depending on the mode of administration, the pharmaceutical composition will preferably comprise from 0.05 to 99.5% by weight, more preferably from 0.1 to 70% by weight, more preferably from 30 to 70% by weight of the active ingredient, and from 0.05 to 99.95% by weight, more preferably from 0.1 to 70% by weight, more preferably from 30 to 70% by weight of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant or preservative.

It is especially advantageous to formulate the pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The compounds of the invention can be administered alone or in combination with a second drug substance.

In another aspect the invention provides:

A combination of a compound of the invention with at least one second drug substance;

A pharmaceutical combination comprising a compound of the invention in combination with at least one second drug substance;

A pharmaceutical composition comprising a compound of the invention in combination with at least one second drug substance and one or more pharmaceutically acceptable excipient(s);

A compound of the invention in combination with at least one second drug substance, e.g. in the form of a pharmaceutical combination or composition, for use in any method as defined herein, e.g.:

A combination, a pharmaceutical combination or a pharmaceutical composition, comprising a compound of the invention and at least one second drug substance for use as a pharmaceutical;

The use as a pharmaceutical of a compound of the invention in combination with at least one second drug substance, e.g. in the form of a pharmaceutical combination or composition;

A method for treating and/or preventing viral infections in a patient in need thereof, comprising co-administering, concomitantly or in sequence, a therapeutically effective amount of a compound of the invention and at least one second drug substance, e.g. in the form of a pharmaceutical combination or composition;

A compound of the invention in combination with at least one second drug substance, e.g. in the form of a pharmaceutical combination or composition, for use in the preparation of a medicament for use in treating and/or preventing viral infections.

The terms "co-administering" or "co-administration" or the like as used herein are meant to encompass administration of the selected second drug substance to a single patient, and are intended to include treatment regimens in which the second drug substance is not necessarily administered by the same route of administration or at the same time. The compound of the invention and any second drug substance may be formulated in separate dosage forms. Alternatively, to decrease the number of dosage forms administered to a patient, the compound of the invention and any second drug substance may be formulated together in any combination. For example, the compound of the invention may be formulated in one dosage form and the second drug substance may be formulated together in another dosage form. Any separate dosage forms may be administered at the same time or different times.

Combinations include fixed combinations, in which a compound of the invention and at least one second drug substance are in the same formulation; kits, in which a compound of the invention and at least one second drug substance in separate formulations are provided in the same package, e.g. with instructions for co-administration; and free combinations in which a compound of the invention and at least one second drug substance are packaged separately, but instructions for concomitant or sequential administration are given.

In another aspect the invention provides:

A pharmaceutical package comprising a first drug substance which is a compound of the invention and at least one second drug substance, beside instructions for combined administration;

A pharmaceutical package comprising a compound of the invention beside instructions for combined administration with at least one second drug substance;

A pharmaceutical package comprising at least one second drug substance beside instructions for combined administration with a compound of the invention.

Treatment with combinations according to the invention may provide improvements compared with single treatment.

In another aspect the invention provides:

A pharmaceutical combination comprising an amount of a compound of the invention and an amount of a second drug substance, wherein the amounts are appropriate to produce a synergistic therapeutic effect;

A method for improving the therapeutic utility of a compound of the invention comprising co-administering, e.g. concomitantly or in sequence, of a therapeutically effective amount of a compound of the invention and a second drug substance;

A method for improving the therapeutic utility of a second drug substance comprising co-administering, e.g. concomitantly or in sequence, of a therapeutically effective amount of a compound of the invention and a second drug substance.

A combination of a compound of the invention and a second drug substance as a combination partner may be administered by any conventional route, for example as set out herein for a compound of the invention. A second drug may be administered in dosages as appropriate, e.g. in dosage ranges which are similar to those used for single treatment, or, e.g. in case of synergy, below conventional dosage ranges.

Pharmaceutical compositions comprising a combination of the invention and pharmaceutical compositions comprising a second drug as described herein, may be provided as appropriate, e.g. according, e.g. analogously, to a method as conventional, or as described herein for a pharmaceutical composition of the invention.

Effective dosages of two or more agents, e.g. a compound of the invention and a second drug substance, are administered together, or in alternation or sequential-step therapy, whereby an effective dosage of each agent is administered serially or sequentially. In general, the first option may typically be preferred over alternation therapy because it induces multiple simultaneous stresses on the virus. The dosages given will depend on absorption, inactivation and excretion rate of the drug as well as other factors. It is to be noted that dosage values will also vary with the severity of the condition to be alleviated. It is to be further understood that for any particular subject, specific dosage regimens and schedules may be adjusted over time according to the individual need and the professional judgment of the person administering or supervising the administration of the compositions.

Daily dosages required in practicing such methods will vary depending upon, for example, the compound of the invention employed, the host, the mode of administration, the severity of the condition to be treated. Suitable daily dosages and unit dosage forms for oral administration to patients are described above. The amount of second drug substance in the dosage form can vary greatly, and can be determined by routine experimentation. For example, the dose of the compound of the invention and the second drug substance are indicated, depending on the pharmacological action required, to be about the same order, e.g. half, that administered for the same compound e.g. on administration alone or with another compound.

By the term "second drug substance" is meant a chemotherapeutic drug that may or may not be a compound of formula (I) or (II), especially any chemotherapeutic agent other than a compound of formula (I) or (II).

For example, a second drug substance as used herein includes, e.g., a drug which has anti-viral activity, especially anti-Flaviviridae activity, most especially anti-dengue or Hepatitis C activity, such as, for example, protease inhibitors, nucleoside/nucleotide analogs, inhibitors of viral entry, viral polymerase inhibitors, immunomodulatory agents, antibodies, and reverse transcriptase inhibitors. Such anti-viral agents include, but are not limited to, ribavirin, vidarabine, acyclovir, ganciclovir, zanamivir, oseltamivir phosphate, famciclovir, atazanavir, amantadine, didanosine, efavirenz, foscarnet, indinavir, lamivudine, nelfinavir, ritonavir, saquinavir, stavudine, valacyclovir, valganciclovir, zidovudine, telbivudine, an interferon, e.g. interferon-α-2a or interferon-α-2b, e.g. Intron® A, Roferon®, Avonex®, Rebif® or Betaferon®, consensus interferon, lymphoblastoid interferon, interferon tau or an interferon conjugated to a water soluble polymer or to human albumin, e.g. albuferon; lamivudine, the compounds disclosed in U.S. Pat. No. 6,812,219 and WO 2004/002422 A2 (the disclosures of which are incorporated herein by reference in their entireties); an anti-fibrotic agent, e.g. a N-phenyl-2-pyrimidine-amine derivative, e.g. imatinib, an immune modulating agent, e.g. mycophenolic acid, a salt or a prodrug thereof, e.g. sodium mycophenolate or mycophenolate mofetil, or a S1P receptor agonist, e.g. FTY720 or an analogue thereof optionally phosphorylated, e.g. as disclosed in EP627406A1, EP778263A1, EP1002792A1, WO02/18395, WO02/76995, WO 02/06268, JP2002316985, WO03/29184, WO03/29205, WO03/62252 and WO03/62248 (the disclosures of which are incorporated herein by reference in their entireties).

Other second drug substances include, but are not limited to, analgesics and anti-inflammatory compounds, e.g. NSAIDs. Examples of other second drug substances include, but are not limited to, paracetamol, aspirin, salsalate, diflunisal, ibuprofen, ketoprofen, nabumetone, piroxicam, naproxen, diclofenac, indomethacin, sulindac, tolmetin, etodolac, ketorolac, oxaprozin and celecoxib; frusemide; vitamin K; bicarbonate; calcium; anti-emetics, e.g. domperidone, metoclopramide, bromopride and alizapride; ranitidine; cimetidine; famotidine; nizatidine; ranitidine; roxatidine; misoprostol; enprostil; esomeprazole; lansoprazole; omeprazole; pantoprazole; rabeprazole; tenatoprazole; carbenoxolone; sucralfate; pirenzepine; anticonvulsants, e.g. acetazolamide, alprazolam, amylobarbitone, carbamazepine, gabapentin, chlordiazepoxide, clobazam, clomethiazole, clonazepam, carbamazepine, diazepam, phenyloin, divalproex, sodium valproate, ethosuximide, flunarizine, fosphenytoin, levetiracetam, lamotrigine, lorazepam, pregabalin, magnesium sulfate, phenobarbitone, midazolam, oxcarbazepine, primidone, vigabatrin, topiramate, valproic acid, valpromide, zonisamide, zopiclone; and oestrogens, e.g. Premarin.

A compound of the invention may, for example, be used in combination with an additional Hepatitis C virus-modulating compound that is or is not of the formula (I) or (II), for treatment of an Hepatitis C virus-associated disorder in a patient.

WO 2005/042020, incorporated herein by reference in its entirety, describes the combination of various Hepatitis C virus inhibitors with a cytochrome P450 ("CYP") inhibitor. Any suitable CYP inhibitor may be used in combination with the compounds of this invention. These CYP inhibitors include, but are not limited to, ritonavir (WO 94/14436, incorporated herein by reference in its entirety), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

Methods for measuring the ability of a compound to inhibit CYP activity are known (see, e.g., U.S. Pat. No. 6,037,157 and Yun, et al. Drug Metabolism & Disposition, vol. 21, pp. 403-407 (1993); incorporated herein by reference). For example, a compound to be evaluated may be incubated with 0.1, 0.5, and 1.0 mg protein/ml, or other appropriate concentration of human hepatic microsomes (e.g., commercially available, pooled characterized hepatic microsomes) for 0, 5, 10, 20, and 30 minutes, or other appropriate times, in the presence of an NADPH-generating system. Control incubations may be performed in the absence of hepatic microsomes for 0 and 30 minutes (triplicate). The samples may be analyzed for the presence of the compound. Incubation conditions that produce a linear rate of compound metabolism will be used a guide for further studies. Experiments known in the art can be used to determine the kinetics of the compound metabolism ($K_m$ and $V_{max}$). The rate of disappearance of compound may be determined and the data analyzed according to Michaelis-Menten kinetics by using Lineweaver-Burk, Eadie-Hofstee, or nonlinear regression analysis.

Inhibition of metabolism experiments may then be performed. For example, a compound (one concentration, $\leq K_m$) may be incubated with pooled human hepatic microsomes in the absence or presence of a CYP inhibitor (such as ritonavir) under the conditions determined above. As would be recognized, control incubations may contain the same concentration of organic solvent as the incubations with the CYP inhibitor. The concentrations of the compound in the samples may be quantitated, and the rate of disappearance of parent compound may be determined, with rates being expressed as a percentage of control activity.

Methods for evaluating the influence of co-administration of a compound of the invention and a CYP inhibitor in a subject are also known (see, e.g., US2004/0028755; incorporated herein by reference). Any such methods could be used in connection with this invention to determine the pharmacokinetic impact of a combination. Subjects that would benefit from treatment according to this invention could then be selected.

Accordingly, one embodiment of this invention provides a method for administering an inhibitor of CYP3A4 and a compound of the invention. Another embodiment of this invention provides a method for administering an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1").

As would be appreciated, CYP3A4 activity is broadly observed in humans. Accordingly, embodiments of this invention involving inhibition of isozyme 3A4 would be expected to be applicable to a broad range of patients.

Accordingly, the invention provides methods wherein the CYP inhibitor is administered together with the compound of the invention in the same dosage form or in separate dosage forms.

As noted above, daily dosages with respect to the second drug substance used will vary depending upon, for example, the compound employed, the host, the mode of administration and the severity of the condition to be treated. For example, lamivudine may be administered at a daily dosage of 100 mg. The pegylated interferon may be administered parenterally one to three times per week, preferably once a week, at a total weekly dose ranging from 2 to 10 million IU, more preferable 5 to 10 million IU, most preferable 8 to 10 million IU. Because of the diverse types of second drug substance that may be used, the amounts can vary greatly, and can be determined by routine experimentation, as described above.

The current standard of care for treating hepatitis C is the combination of pegylated interferon alpha with ribavirin, of which the recommended doses are 1.5 µg/kg/wk peginterferon alfa-2b or 180 µg/wk peginterferon alfa-2a, plus 1000 to 1200 mg daily of ribavirin for 48 weeks for genotype I patients, or 800 mg daily of ribavirin for 24 weeks for genotype ⅔ patients. The compound of the invention and a second drug substance may be administered by any conventional route, in particular enterally, e.g. orally, for example in the form of solutions for drinking, tablets or capsules or parenterally, for example in the form of injectable solutions or suspensions.

Conjugates of interferon to a water-soluble polymer are meant to include especially conjugates to polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917,888, European Patent Application No. 0 236 987, European Patent Application No. 0 510 356 and International Application Publication No. WO 95/13090, the disclosures of which are incorporated herein by reference in their entireties. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

Especially preferred conjugates of interferon are pegylated alfa-interferons, for example pegylated interferon-α-2a, pegylated interferon-α-2b; pegylated consensus interferon or pegylated purified interferon-α product. Pegylated interferon-α-2a is described e.g. in European Patent 593,868 (incorporated herein by reference in its entirety) and commercially available e.g. under the tradename PEGASYS® (Hoffmann-La Roche). Pegylated interferon-α-2b is described, e.g. in European Patent 975,369 (incorporated herein by reference in its entirety) and commercially available e.g. under the tradename PEG-INTRON A® (Schering Plough). Pegylated consensus interferon is described in WO 96/11953 (incorporated herein by reference in its entirety). The preferred pegylated α-interferons are pegylated interferon-α-2a and pegylated interferon-α-2b. Also preferred is pegylated consensus interferon.

Other preferred second drug substances include fusion proteins of an interferon, for example fusion proteins of interferon-α-2a, interferon-α-2b; consensus interferon or purified interferon-α product, each of which is fused with another protein. Certain preferred fusion proteins comprise an interferon (e.g., interferon-α-2b) and an albumin as described in U.S. Pat. No. 6,973,322 and international publications WO02/60071, WO05/003296 and WO05/077042 (Human Genome Sciences). A preferred interferon conjugated to a human albumin is Albuferon (Human Genome Sciences).

Cyclosporins which bind strongly to cyclophilin but are not immunosuppressive include those cyclosporins recited in U.S. Pat. Nos. 5,767,069 and 5,981,479 and are incorporated herein by reference. [Melle]$^4$-cyclosporin is a preferred non-immunosuppressive cyclosporin. Certain other cyclosporin derivatives are described in WO2006039668 (Scynexis) and WO2006038088 (Debiopharm SA) and are incorporated herein by reference. A cyclosporin is considered to be non-immunosuppressive when it has an activity in the Mixed Lymphocyte Reaction (MLR) of no more than 5%, preferably no more than 2%, that of cyclosporin A. The Mixed Lymphocyte Reaction is described by T. Meo in "Immunological Methods", L. Lefkovits and B. Peris, Eds., Academic Press, N.Y. pp. 227-239 (1979). Spleen cells (0.5×10$^6$) from Balb/c mice (female, 8-10 weeks) are co-incubated for 5 days with 0.5×10$^6$ irradiated (2000 rads) or mitomycin C treated spleen cells from CBA mice (female, 8-10 weeks). The irradiated allogeneic cells induce a proliferative response in the Balb/c spleen cells which can be measured by labeled precursor incorporation into the DNA. Since the stimulator cells are irradiated (or mitomycin C treated) they do not respond to the Balb/c cells with proliferation but do retain their antigenicity. The IC$_{50}$ found for the test compound in the MLR is compared with that found for cyclosporin A in a parallel experiment. In addition, non-immunosuppressive cyclosporins lack the capacity of inhibiting CN and the downstream NF-AT pathway. [Melle]$^4$-cyclosporin is a preferred non-immunosuppressive cyclophilin-binding cyclosporin for use according to the invention.

Ribavirin (1-β-D-ribofuranosyl-1-1,2,4-triazole-3-caroxamide) is a synthetic, non-interferon-inducing, broad spectrum antiviral nucleoside analog sold under the trade name Virazole (The Merck Index, 11$^{th}$ edition, Editor: Budavar, S, Merck & Co., Inc., Rahway, N.J., p 1304, 1989). U.S. Pat. No. 3,798,209 and RE29,835 (incorporated herein by reference in their entireties) disclose and claim ribavirin. Ribavirin is structurally similar to guanosine, and has in vitro activity against several DNA and RNA viruses including Flaviviridae (Gary L. Davis, Gastroenterology 118:S104-S114, 2000).

Other combinations include those of a compound of the invention with a non-immunosuppressive cyclophilin-binding cyclosporine, with mycophenolic acid, a salt or a prodrug thereof, and/or with a S1P receptor agonist, e.g. FTY720.

Additional examples of second drug substances that can be used in combination with a compound of the invention include:

(1) Interferons, including interferon alpha 2a or 2b and pegylated (PEG) interferon alpha 2a or 2b, for example:
(a) Intron-A®, interferon alfa-2b (Schering Corporation, Kenilworth, N.J.);
(b) PEG-Intron®, peginteferon alfa-2b (Schering Corporation, Kenilworth, N.J.);
(c) Roferon®, recombinant interferon alfa-2a (Hoffmann-La Roche, Nutley, N.J.);
(d) Pegasys®, peginterferon alfa-2a (Hoffmann-La Roche, Nutley, N.J.);
(e) Berefor®, interferon alfa 2 available (Boehringer Ingelheim Pharmaceutical, Inc., Ridgefield, Conn.);
(f) Sumiferon®, a purified blend of natural alpha interferons (Sumitomo, Japan)
(g) Wellferon®, lymphoblastoid interferon alpha n1 (GlaxoSmithKline);
(h) Infergen®, consensus alpha interferon (InterMune Pharmaceuticals, Inc., Brisbane, Calif.);
(i) Alferon®, a mixture of natural alpha interferons (Interferon Sciences, and Purdue Frederick Co., CT);
(j) Viraferon®;
(k) Consensus alpha interferon from Amgen, Inc., Newbury Park, Calif.

Other forms of interferon include: interferon beta, gamma, tau and omega, such as Rebif (Interferon beta 1a) by Serono, Omniferon (natural interferon) by Viragen, REBIF (interferon beta-1a) by Ares-Serono, Omega Interferon by Bio-Medicines; oral Interferon Alpha by Amarillo Biosciences; an interferon conjugated to a water soluble polymer or to a human albumin, e.g., Albuferon (Human Genome Sciences), an antiviral agent, a consensus interferon, ovine or bovine interferon-tau.

Conjugates of interferon to a water-soluble polymer are meant to include especially conjugates to polyalkylene oxide homopolymers such as polyethylene glocol (PEG) or polypropylene glycols, polyoxyethylenated polyols, copolymers thereof and block copolymers thereof. As an alternative to polyalkylene oxid-based polymers, effectively non-antigenic materials such as dextran, polyvinyl pyrrolidones, polyacrylamides, polyvinyl alcohols, carbohydrate-based polymers and the like can be used. Since the polymeric modification sufficiently reduces antigenic response, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

(2) Ribavirin, such as ribavirin (1-beta-D-ribofuranosyl-1H-1,2,4-triazole-3-carboxamide) from Valeant Pharmaceuticals, Inc., Costa Mesa, Calif.); Rebetol® from Schering Corporation, Kenilworth, N.J., and Copegus® from Hoffmann-La Roche, Nutley, N.J.; and new ribavirin analogues in development such as Levovirin and Viramidine by Valeant.

(3) Thiazolidine derivatives which show relevant inhibition in a reverse-phase HPLC assay with an NS3/4A fusion protein and NS5A/5B substrate (Sudo K. et al., *Antiviral Research,* 1996, 32, 9-18), especially compound RD-1-6250, possessing a fused cinnamoyl moiety substituted with a long alkyl chain, RD4 6205 and RD4 6193.

(4) Thiazolidines and benzanilides identified in Kakiuchi N. et al. *J. FEBS Letters* 421, 217-220; Takeshita N. et al. *Analytical Biochemistry,* 1997, 247, 242-246.

(5) A phenanthrenequinone possessing activity against protease in a SDS-PAGE and autoradiography assay isolated from the fermentation culture broth of *Streptomyces* sp., Sch 68631 (Chu M. et al., Tetrahedron Letters, 1996, 37, 7229-7232), and Sch 351633, isolated from the fungus *Penicillium griseofulvum,* which demonstrates activity in a scintillation proximity assay (Chu M. et al, *Bioorganic and Medicinal Chemistry Letters* 9, 1949-1952).

(6) Protease inhibitors; examples include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al, Preparation and use of amino acid derivatives as anti-viral agents, German Patent Pub. DE 19914474; Tung et al. Inhibitors of serine proteases, particularly hepatitis C virus NS3 protease; PCT WO 98/17679), including alphaketoamides and hydrazinoureas, and inhibitors that terminate in an electrophile such as a boronic acid or phosphonate (Llinas-Brunet et al. Hepatitis C inhibitor peptide analogues, PCT WO 99/07734) are being investigated.

Non-substrate-based NS3 protease inhibitors such as 2,4,6-trihydroxy-3-nitro-benzamide derivatives (Sudo K. et al., *Biochemiscal and Biophysical Research Communications,* 1997, 238 643-647; Sudo K. et al. *Antiviral Chemistry and Chemotherapy,* 1998, 9, 186), including RD3-4082 and RD3-4078, the former substituted on the amide with a 14 carbon chain and the latter processing a para-phenoxyphenyl group are also being investigated.

Sch 68631, a phenanthrenequinone, is an Hepatitis C virus protease inhibitor (Chu M et al., *Tetrahedron Letters* 37:7229-7232, 1996). In another example by the same authors, Sch 351633, isolated from the fungus *Penicillium grieofulvum,* was identified as a protease inhibitor (Chu M. et al., *Bioorganic and Medicinal Chemistry Letters* 9:1949-1952). Nanomolar potency against the Hepatitis C virus NS3 protease enzyme has been achieved by the design of selective inhibitors based on the macromolecule eglin c. Eglin c, isolated from leech, is a potent inhibitor of several serine proteases such as *S. griseus* proteases A and B, ∀-chymotrypsin, chymase and subtilisin. Qasim M. A. et al., *Biochemistry* 36:1598-1607, 1997.

U.S. patents disclosing protease inhibitors for the treatment of Hepatitis C virus include, for example, U.S. Pat. No. 6,004,933 to Spruce et al (incorporated herein by reference in its entirety) which discloses a class of cysteine protease inhibitors for inhibiting Hepatitis C virus endopeptidase 2; U.S. Pat. No. 5,990,276 to Zhang et al. (incorporated herein by reference in its entirety) which discloses synthetic inhibitors of hepatitis C virus NS3 protease; U.S. Pat. No. 5,538,865 to Reyes et al. (incorporated herein by reference in its entirety). Peptides as NS3 serine protease inhibitors of Hepatitis C virus are disclosed in WO 02/008251 to Corvas International, Inc., and WO 02/08187 and WO 02/008256 to Schering Corporation (incorporated herein by reference in their entireties). Hepatitis C virus inhibitor tripeptides are disclosed in U.S. Pat. Nos. 6,534,523, 6,410,531 and 6,420,380 to Boehringer Ingelheim and WO 02/060926 to Bristol Myers Squibb (incorporated herein by reference in their entireties). Diaryl peptides as NS3 serine protease inhibitors of Hepatitis C virus are disclosed in WO 02/48172 to Schering Corporation (incorporated herein by reference). Imidazoleidinones as NS3 serine protease inhibitors of Hepatitis C virus are disclosed in WO 02/18198 to Schering Corporation and WO 02/48157 to Bristol Myers Squibb (incorporated herein by reference in their entireties). WO 98/17679 to Vertex Pharmaceuticals and WO 02/48116 to Bristol Myers Squibb also disclose Hepatitis C virus protease inhibitors (incorporated herein by reference in their entireties).

Hepatitis C virus NS3-4A serine protease inhibitors including BILN 2061 by Boehringer Ingelheim, VX-950 by Vertex, SCH 6/7 by Schering-Plough, and other compounds currently in preclinical development.

Substrate-based NS3 protease inhibitors, including alpha-ketoamides and hydrazinoureas, and inhibitors that terminate in an elecrophile such as a boronic acid or phosphonate; Non-substrate-based NS3 protease inhibitors such as 2,4,6-trihydroxy-3-nitro-benzamide derivatives including RD3-4082 and RD3-4078, the former substituted on the amide with a 14 carbon chain and the latter processing a para-phenoxyphenyl group; and Sch68631, a phenanthrenequinone, an Hepatitis C virus protease inhibitor.

Sch 351633, isolated from the fungus *Penicillium griseofulvum* was identified as a protease inhibitor. Eglin c, isolated from leech is a potent inhibitor of several serine proteases such as *S. griseus* proteases A and B, a-chymotrypsin, chymase and subtilisin.

U.S. Pat. No. 6,004,933 (incorporated herein by reference in its entirety) discloses a class of cysteine protease inhibitors from inhibiting Hepatitis C virus endopeptidase 2; synthetic inhibitors of Hepatitis C virus NS3 protease; Hepatitis C virus inhibitor tripeptides; diaryl peptides such as NS3 serine protease inhibitors of Hepatitis C virus; imidazolidindiones as NS3 serine protease inhibitors of Hepatitis C virus.

Thiazolidines and benzanilides. Thiazolidine derivatives which show relevant inhibition in a reverse-phase HPLC assay with an NS3/4A fusion protein and NS5A/5B substrate especially compound RD-16250 possessing a fused cinnamoyl moiety substituted with a long alkyl chain, RD4 6205 and RD4 6193

Phenanthrenequinone possessing activity against protease in a SDS-PAGE and autoradiography assay isolated from the fermentation culture broth of *Streptomyces* sp, Sch68631 and Sch351633, isolated from the fungus *Penicillium griseofulvum,* which demonstrates activity in a scintillation proximity assay.

(7) Nucleoside or non-nucleoside inhibitors of Hepatitis C virus NS5B RNA-dependent RNA polymerase, such as 2'-C-methyl-3'-O-L-valine ester ribofuranosyl cytidine (Idenix) as disclosed in WO 2004/002422 A2 (incorporated herein by reference in its entirety), R803 (Rigel), JTK-003 (Japan Tabacco), HCV-086 (ViroPharma/Wyeth) and other compounds currently in preclinical development;
gliotoxin and the natural product cerulenin;
2'-fluoronucleosides;

other nucleoside analogues as disclosed in WO 02/057287 A2, WO 02/057425 A2, WO 01/90121, WO 01/92282, and U.S. Pat. No. 6,812,219, the disclosures of which are incorporated herein by reference in their entirety.

Idenix Pharmaceuticals discloses the use of branched nucleosides in the treatment of flaviviruses (including Hepatitis C virus) and pestiviruses in International Publication Nos. WO 01/90121 and WO 01/92282 (incorporated herein by reference in their entireties). Specifically, a method for the treatment of hepatitis C infection (and flaviviruses and pestiviruses) in humans and other host animals is disclosed in the Idenix publications that includes administering an effective amount of a biologically active 1', 2', 3' or 4'-branched β-D or β-L nucleosides or a pharmaceutically acceptable salt or prodrug thereof, administered either alone or in combination with another antiviral agent, optionally in a pharmaceutically acceptable carrier. Certain preferred biologically active 1', 2', 3', or 4' branched β-D or β-L nucleosides, including Telbivudine, are described in U.S. Pat. Nos. 6,395,716 and 6,875,751, each of which are incorporated herein by reference.

Other patent applications disclosing the use of certain nucleoside analogs to treat hepatitis C virus include: PCTCA00/01316 (WO 01/32153; filed Nov. 3, 2000) and PCT/CA01/00197 (WO 01/60315; filed Feb. 19, 2001) filed by BioChem Pharma, Inc., (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd. (the disclosures of which are incorporated herein by reference in their entireties).

PCT Publication No. WO 99/43691 to Emory University (incorporated herein by reference in its entirety), entitled "2'-Fluoronucleosides" discloses the use of certain 2'-fluoronucleosides to treat Hepatitis C virus.

Eldrup et al. (Oral Session V, Hepatitis C Virus, Flaviviridae; 16th International Conference on Antiviral Research (Apr. 27, 2003, Savannah, Ga.)) describes the structure activity relationship of 2'-modified nucleosides for inhibition of Hepatitis C virus.

Bhat et al. (Oral Session V, Hepatitis C Virus, Flaviviridae, 2003 (Oral Session V, Hepatitis C Virus, Flaviviridae; 16th International conference on Antiviral Research (Apr. 27, 2003, Savannah, Ga.); p A75) describes the synthesis and pharmacokinetic properties of nucleoside analogues as possible inhibitors of Hepatitis C virus RNA replication. The authors report that 2'-modified nucleosides demonstrate potent inhibitory activity in cell-based replicon assays.

Olsen et al. (Oral Session V, Hepatitis C Virus, Flaviviridae; 16th International Conference on Antiviral Research (Apr. 27, 2003, Savannah, Ga.) p A76) also describe the effects of the 2'-modified nucleosides on Hepatitis C virus RNA replication.

(8) Nucleotide polymerase inhibitors and gliotoxin (Ferrari R. et al. *Journal of Virology,* 1999, 73, 1649-1654), and the natural product cerulenin (Lohmann V. et al. *Virology,* 1998, 249, 108-118).

(9) Hepatitis C virus NS3 helicase inhibitors, such as VP_50406 by ViroPharma and compounds from Vertex. Other helicase inhibitors (Diana G. D. et al., Compounds, compositions and methods for treatment of hepatitis C, U.S. Pat. No. 5,633,358 (incorporated herein by reference in its entirety); Diana G. D. et al., Piperidine derivatives, pharmaceutical compositions thereof and their use in the treatment of hepatitis C, WO 97/36554).

(10) Antisense phosphorothioate oligodeoxynucleotides (S-ODN) complementary to sequence stretches in the 5' non-coding region (NCR) of the virus (Alt M. et al., *Hepatology,* 1995, 22, 707-717), or nucleotides 326-348 comprising the 3' end of the NCR and nucleotides 371-388 located in the core coding region of the Hepatitis C virus RNA (Alt M. et al., *Archives of Virology,* 1997, 142, 589-599; Galderisi U. et al., *Journal of Cellular Physiology,* 199, 181, 251-257); such as ISIS 14803 by Isis Pharm/Elan, antisense by Hybridon, antisense by AVI bioPharma.

(11) Inhibitors of IRES-dependent translation (Ikeda N et al., Agent for the prevention and treatment of hepatitis C, Japanese Patent Pub. JP-08268890; Kai Y et al. Prevention and treatment of viral diseases, Japanese Patent Pub. JP-10101591); such as ISIS 14803 by Isis Pharm/Elan, IRES inhibitor by Anadys, IRES inhibitors by Immusol, targeted RNA chemistry by PTC Therapeutics.

(12) Ribozymes, such as nuclease-resistant ribozymes (Maccjak, D. J. et al., *Hepatology* 1999, 30, abstract 995) and those directed in U.S. Pat. No. 6,043,077 to Barber et al., and U.S. Pat. Nos. 5,869,253 and 5,610,054 to Draper et al. (incorporated herein by reference in their entireties) for example, HEPTAZYME by RPI.

(13) siRNA directed against Hepatitis C virus genome.

(14) Hepatitis C virus replication inhibitor of any other mechanisms such as by VP50406ViroPharama/Wyeth, inhibitors from Achillion, Arrow.

(15) An inhibitor of other targets in the Hepatitis C virus life cycle including viral entry, assembly and maturation.

(16) An immune modulating agent such as an IMPDH inhibitor, mycophenolic acid, a salt or a prodrug thereof sodium mycophenolate or mycophenolate mofetil, or Merimebodib (VX-497); thymosin alpha-1 (Zadaxin, by SciClone); or a S1P receptor agonist, e.g. FTY720 or analogue thereof optionally phosphorylated.

(17) An anti-fibrotic agent, such as a N-phenyl-2-pyrimidine-amine derivative, imatinib (Glivec), IP-501 by Indevus, and Interferon gamma 1b from InterMune.

(18) Therapeutic vaccine by Intercell, Epimmune/Genecor, Merix, Tripep (Chron-VacC), immunotherapy (Therapore) by Avant, T cell therapy by CellExSys, monoclonal antibody XTL-002 by STL, ANA 246 and ANA 246 BY Anadys.

(19) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), amantadine, bile acids (U.S. Pat. No. 5,846,99964 to Ozeki et al.), N-(phosphonoacetyl)-L-aspartic acid,) U.S. Pat. No. 5,830,905 to Diana et al.), benzenedicarboxamides (U.S. Pat. No. 5,633,388 to Diane et al.), polyadenylic acid derivatives (U.S. Pat. No. 5,496,546 to Wang et al.), 2'3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961) and piperidines (U.S. Pat. No. 5,830,905 to Diana et al.); the disclosures of which are incorporated herein by reference in their entireties. Also, squalene, telbivudine, N-(phosphonoacetyl)-L-aspartic acid, benzenedicarboxamides, polyadenylic acid derivatives, glycosylation inhibitors, and nonspecific cytoprotective agents that block cell injury caused by the virus infection.

(20) Any other compound currently in preclinical or clinical development for the treatment of Hepatitis C virus, including Interleukin-10 (Schering-Plough), AMANTADINE (Symmetrel) by Endo Labs Solvay, caspase inhibitor IDN- 6556 by Idun Pharma, HCV/MF59 by Chiron, CIVACIR (Hepatitis C Immune Globulin) by NABI, CEPLENE (histamine dichloride) by Maxim, IDN-6556 by Idun PHARM, T67, a beta-tubulin inhibitor, by Tularik, a therapeutic vaccine directed to E2 by Innogenetics, FK788 by Fujisawa Healthcare, IdB1016 (Siliphos, oral silybin-phosphatidyl choline phytosome), fusion inhibitor by Trimeris, Dication by Immtech, hemopurifier by Aethlon Medical, UT 231B by United Therapeutics.

(21) Purine nucleoside analog antagonists of TIR7 (toll-like receptors) developed by Anadys, e.g., Isotorabine (ANA245) and its prodrug (ANA975), which are described in European applications EP348446 and EP636372, International Publications WO03/045968, WO05/121162 and WO05/25583, and U.S. Pat. No. 6,973,322, each of which is incorporated by reference.

(21) Non-nucleoside inhibitors developed by Genelabs and described in International Publications WO2004/108687, WO2005/12288, and WO2006/076529, each of which is incorporated herein by reference.

(22) Other second drug substances (e.g., non-immunomodulatory or immunomodulatory compounds) that may be used in combination with a compound of this invention include, but are not limited to, those specified in WO 02/18369, which is incorporated herein by reference.

In another aspect, this invention provides a method comprising administering a compound of the invention and another anti-viral agent, preferably an anti-Flaviviridae, e.g. and anti-dengue or anti-Hepatitis C virus agent. Such anti-viral agents include, but are not limited to, immunomodulatory agents, such as α, β, and δ interferons, pegylated derivatized interferon-a compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the Flaviviridae (e.g. dengue virus, Hepatitis C virus) life cycle, including helicase, polymerase, and metalloprotease inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

Each component of a combination according to this invention may be administered separately, together, or in any combination thereof. As recognized by skilled practitioners, dosages of interferon are typically measured in IU (e.g., about 4 million IU to about 12 million IU). Each component may be administered in one or more dosage forms. Each dosage form may be administered to the patient in any order.

It will be appreciated that any of the sub-scopes disclosed herein e.g. with respect to X, R1, R2, R3, R4, R5, R6 and/or R7 may be combined with any of the other sub-scopes disclosed herein to produce further sub-scopes.

The following general methods may be used to prepare compounds of formula (I) and (II). The preparation of specific compounds of the invention will be apparent to those skilled in the art by reference to the particular Examples described below. Insofar as any particular process is not specifically described herein, this may be carried out in conventional or known manner or in a manner analogous to known methods.

General Procedure 1

Intermediate compound I-4 may be prepared according the General Procedure 1, and coupled to any suitable base moiety to give a compound of the invention. General Procedure 1 uses a diprotected (at the 4-hydroxyl and 5-hydroxymethyl substituents) 4-hydroxyl-5-hydroxymethyl-2-methoxy-tetrahydrofuran-3-acetate such as (3R,4R,5R)-4-(2,4-dichlorobenzyloxy)-5-(2,4-dichlorobenzyloxymethyl)-2-methoxy-tetrahydrofuran-3-acetate as starting material. The acetate group is removed under basic conditions, for example using NaOMe or another suitable base such as, for example, sodium alkoxide or potassium carbonate. The oxidation step may be carried out using any suitable oxidizing agent/conditions such as, e.g., Swern Oxidation, TEMPO or Dess-Martin periodinane, to give the furan-3-one. Conversion to the alkynylene moiety may be effected using a suitable Grignard reagent such as an alkynylmagnesium halide, e.g. alkynylmagnesium bromide such as ethynyl magnesium bromide, or with an organolithium reagent such as an alkynyl lithium reagent, e.g. ethynyl lithium. Compound I-4 may be coupled to any suitable base moiety, such as, for example an adenine or guanine derivative, where X=N, CH or CR4, R1'=halogen, NR5R6 or OR7, R2'=H, halogen or NR5R6 and R3, R4, R5, R6 and R7 are as defined herein. In some examples, X may be CH. In other examples X may be CR4. In some examples R4 may be halogen, e.g. F or I. In other examples R4 may be alkynyl, e.g. ethynyl. In some examples R1' may be halogen, e.g. Cl. In other examples, R1' may be amino or alkoxy, e.g. methoxy. In some examples R2' may be H. Other examples of bases/base analogs include, e.g., 4-chloro-7H-pyrrolo[2,3-d]pyrimidine, 4-chloro-5-fluoro-pyrrolo[2,3-d]pyrimidine, 4-chloro-5-iodo-pyrrolo[2,3-d]pyrimidine, 7H-pyrrolo[2,3-d]pyrimidin-4-yl-isoindole-1,3-dione and 4-chloro-5-acetylene-pyrrolo[2,3-d]pyrimidine. The protecting groups may be removed e.g. using suitable Lewis acid such as $BCl_3$ to give the desired nucleoside analog.

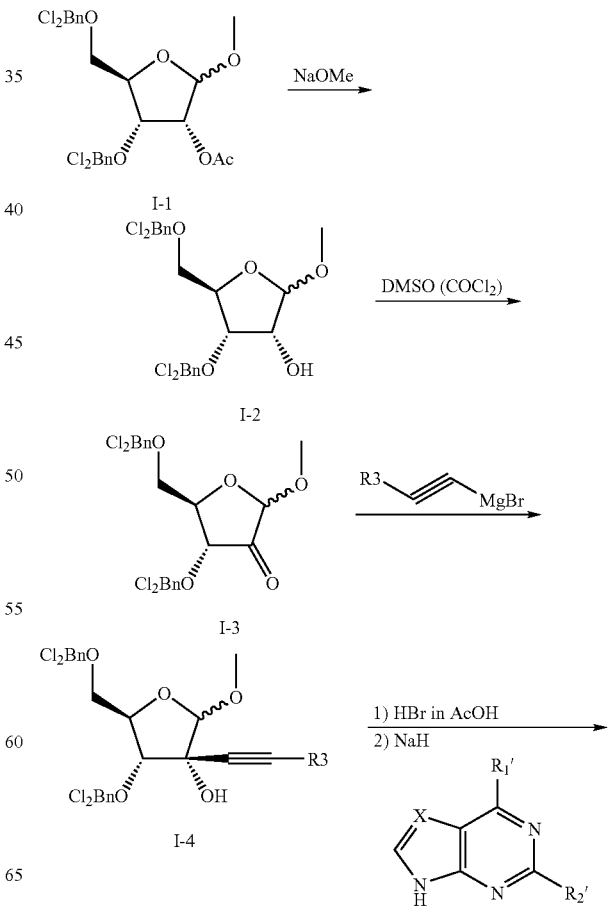

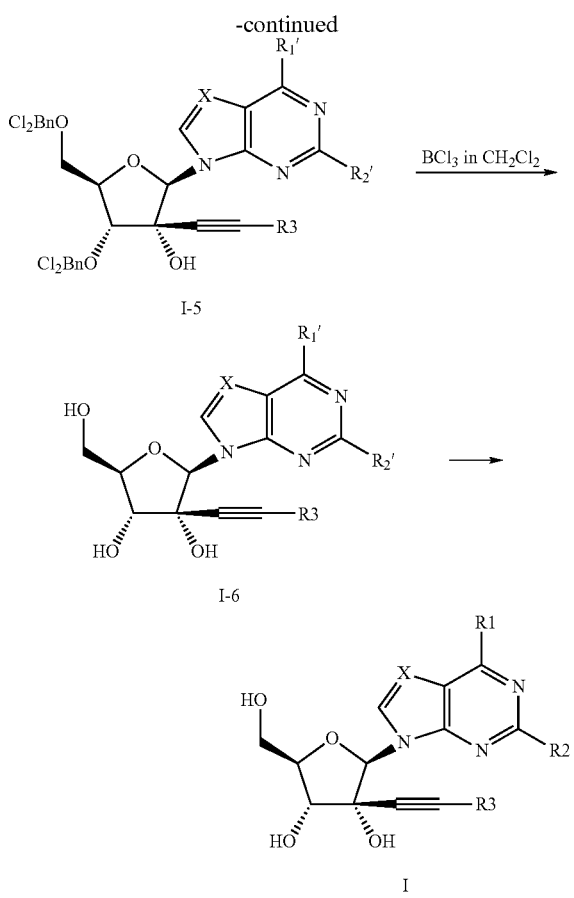

R1, R2 and R3 are as defined herein

General Procedure 1 Step 1: (3R,4S,5R)-5-(2,4-Dichlorobenzyloxymethyl)-4-(2,4-dichlorobenzyloxy)-2-methoxy-tetrahydrofuran-3-ol (I-2)

To a solution of (3R,4R,5R)-5-(2,4-dichloro-benzyloxymethyl)-4-(2,4-dichlorobenzyloxy)-2-methoxy-tetrahydrofuran-3-acetate I-1 (10 g, 19.1 mmol) in MeOH (150 ml) is added a solution of 30% NaOMe in MeOH (5.37 ml, 28.6 mmol, 1.5 equiv.) and the reaction is stirred at room temperature for 30 mins. The reaction mixture is concentrated and dissolved in ethyl acetate (180 ml), washed with 1 N HCl solution and saturated brine, dried (anhyd $Na_2SO_4$) and concentrated to give (3R,4S,5R)-5-(2,4-Dichlorobenzyloxymethyl)-4-(2,4-dichlorobenzyloxy)-2-methoxy-tetrahydrofuran-3-ol I-2 as yellowish oil. The obtained crude compound is used for the next step without further purification.

General Procedure 1 Step 2: (4R,5R)-5-(2,4-Dichlorobenzyloxymethyl)-4-(2,4-dichlorobenzyloxy)-2-methoxy-dihydrofuran-3-one (I-3)

To a cooled solution of oxalyl chloride (2.15 ml, 25.1 mmol, 1.3 equiv.) in DCM (20 ml) at −78° C. is added a solution of DMSO (2.85 ml, 36.5 mmol, 1.9 equiv.) in DCM (30 ml) and stirred at −78° C. for 30 mins. Then a solution of (3R,4S,5R)-5-(2,4-Dichlorobenzyloxymethyl)-4-(2,4-dichlorobenzyloxy)-2-methoxy-tetrahydrofuran-3-ol I-2 (9.6 g, 18.8 mmol, 1 equiv.) in DCM (50 ml) is added slowly and stirred at −78° C. for about 2 h. After that, triethylamine (15.8 ml, 114 mmol, 6.0 equiv.) is added to the reaction mixture and slowly brought to room temperature and stirred for 1 h. After the reaction is completed, the mixture is diluted with water (100 ml) and DCM (50 ml). The DCM layer is separated and washed with 1 N HCl solution and saturated brine, dried (anhyd $Na_2SO_4$), concentrated and purified by flash chromatography (hexane:ethyl acetate=70:30) to give (4R,5R)-5-(2,4-Dichlorobenzyloxymethyl)-4-(2,4-dichlorobenzyloxy)-2-methoxy-dihydrofuran-3-one I-3 as slightly yellow oil.

General Procedure 1 Step 3: (3R,4R,5R)-5-(2,4-Dichlorobenzyloxymethyl)-4-(2,4-dichlorobenzyloxy)-3-ethynyl-2-methoxy-tetrahydrofuran-3-ol (I-4)

To a cold (0° C.) solution of 0.5M ethynylmagnesium bromide (R3=—H) in THF (137.5 ml, 68.5 mmol, 5 equiv.) is added a solution of (4R,5R)-5-(2,4-Dichlorobenzyloxymethyl)-4-(2,4-dichlorobenzyloxy)-2-methoxy-dihydrofuran-3-one I-3 (6.6 g 13.7 mmol, 1 equiv.) in THF (15 ml) and stirred at the same temperature for 3 h. The reaction mixture is quenched with cold saturated $NH_4Cl$ (50 ml) and extracted with ethyl acetate (2×60 mL). The organic layer is washed with 1 N HCl solution and saturated brine, dried (anhyd $Na_2SO_4$), concentrated and purified by flash chromatography (hexane:ethyl acetate=85:15) to give (3R,4R,5R)-5-(2,4-Dichlorobenzyloxymethyl)-4-(3,5-dichlorobenzyloxy)-3-ethynyl-2-methoxy-tetrahydrofuran-3-ol I-4 as a yellowish form.

General Procedure 1 Step 4: (2R,3R,4R,5R)-2-(4-Chloro-pyrrolo[2,3-d]pyrimidin-7-yl)-4-(2,4-dichlorobenzyloxy)-5-(2,4-dichlorobenzyloxymethyl)-3-ethynyl-tetrahydrofuran-3-ol (I-5)

To a solution of (3R,4R,5R)-5-(2,4-dichlorobenzyloxymethyl)-4-(2,4-dichlorobenzyloxy)-3-ethynyl-2-methoxy-tetrahydrofuran-3-ol I-4 (500 mg, 1 mmol, 1 equiv.) in dry DCM (5 ml) is added solution of 33% HBr-AcOH (0.88 mL, 5 mmol, 5 equiv.) and stirred at r. t. for 1.5 h. After the starting material is consumed, the reaction mixture is evaporated under vacuum (1 mbar, 35° C.) to obtain the bromide intermediate as a thick oil. It is then dissolved in dry acetonitrile (10 ml). In another flask, to a mixture of 4-chloropyrrolo[2,3-d]pyrimidine ($R_1'$=Cl, $R_2'$=H, X=CH) (153.0 mg, 1 mmol, 1 equiv.) and NaH (200 mg, 5 mmol, 5 equiv.) in acetonitrile (15 ml) previously stirred for 0.5 h at room temperature is added the solution of bromide intermediate obtained above, and the reaction mixture is stirred at room temperature for 18 h. The solvent is removed and diluted with ethyl acetate (60 ml), washed with water, brine, dried (anhyd $Na_2SO_4$) and concentrated to give a thick liquid. The crude product is purified by flash chromatography (hexane:ethyl acetate=80:20) to give (2R,3R,4R,5R)-2-(4-Chloro-pyrrolo[2,3-d]pyrimidin-7-yl)-4-(2,4-dichlorobenzyloxy)-5-(2,4-dichlorobenzyloxymethyl)-3-ethynyl-tetrahydrofuran-3-ol I-5 as slightly yellow solid.

General Procedure 1 Step 5: (2R,3R,4R,5R)-2-(4-Chloro-pyrrolo[2,3-d]pyrimidin-7-yl)-3-ethynyl-5-hydroxymethyl-tetrahydro-furan-3,4-diol (I-6)

To a cold (−78° C.) solution of (2R,3R,4R,5R)-2-(4-Chloro-pyrrolo[2,3-d]pyrimidin-7-yl)-4-(2,4-dichlorobenzyloxy)-5-(2,4-dichlorobenzyloxymethyl)-3-ethynyl-tetrahydrofuran-3-ol I-5 (150 mg, 0.24 mmol, 1 equiv.) in dry DCM (20 ml) is added 1M solution of BCl₃ in DCM (2.4 ml, 2.4 mmol, 10 equiv.) drop-wise and stirred at −78° C. for about 5 h. The reaction mixture is quenched with MeOH (15 mL) at 0° C. and stirred for 30 min. Solvent is evaporated and dried together with silica gel (4 ml), the crude product on silica gel is purified by flash chromatography (DCM:methanol=90:10) to give (2R,3R,4R,5R)-2-(4-Chloro-pyrrolo[2,3-d]pyrimidin-7-yl)-3-ethynyl-5-hydroxymethyl-tetrahydrofuran-3,4-diol I-6 as a brown foam.

General Procedure 1 Step 6: (2R,3R,4R,5R)-2-(4-Amino-pyrrolo[2,3-d]pyrimidin-7-yl)-3-ethynyl-5-hydroxymethyl-tetrahydrofuran-3,4-diol (I)

A mixture of (2R,3R,4R,5R)-2-(4-Chloro-pyrrolo[2,3-d]pyrimidin-7-yl)-3-ethynyl-5-hydroxymethyl-tetrahydrofuran-3,4-diol 1-6 (96 mg, 0.31 mmol, 1 equiv.) and NH₃.H₂O (R1=NH₂) (10 mL of 28-30% ammonia in water) in a glass pressure tube is heated at 100° C. for 5 h. The reaction mixture is concentrated to dry and purified by preparative HPLC with a gradient of acetonitrile in water from 0% to 35% in 30 mins. The pure fractions are combined and lyophilized to give (2R,3R,4R,5R)-2-(4-amino-pyrrolo[2,3-d]pyrimidin-7-yl)-3-ethynyl-5-hydroxymethyl-tetrahydrofuran-3,4-diol (X=CH, R1=NH₂, R2=H, R3=H) I as slight yellow foam.

General Procedure 2: Preparation of the Intermediate diprotected (at the 4-hydroxyl and 5-hydroxymethyl substituents)-(3R,4R,5R)-3-alkynyl-5-hydroxymethyl-tetrahydrofuran-2,3,4-triol (II-1)

Intermediate compound II-1 can be prepared according to General Procedure 2a, 2b or 2c as described below.

General Procedure 2a uses a diprotected (at the 4-hydroxyl and 5-hydroxymethyl substituents) 4-hydroxyl-5-hydroxymethyl-2-methoxy-tetrahydrofuran-3-acetate such as (3R,4R,5R)-4-(2,4-dichlorobenzyloxy)-5-(2,4-dichlorobenzyloxymethyl)-2-methoxy-tetrahydro-furan-3-acetate as starting material. The acetate group is removed under basic conditions, for example using NaOMe or another suitable base such as, for example, sodium alkoxide, potassium carbonate etc. The oxidation step may be carried out using any suitable oxidizing agent/conditions such as, e.g., Swern Oxidation, TEMPO or Dess-Martin periodinane to give the furan-3-one. Conversion to the alkynylene moiety may be effected using a suitable Grignard reagent such as an alkynylmagnesium halide, e.g. alkynylmagnesium bromide such as ethynyl magnesium bromide, or with an organolithium reagent such as an alkynyl lithium reagent, e.g. ethynyl lithium.

General Procedure 2b uses a triprotected (at the 2-hydroxyl, 4-hydroxyl and 5-hydroxymethyl substituents) tetrahydrofuran-3-ol such as 1,3,5-tri-O-benzoyl-α-D-ribofuranose as starting material. The oxidation step may be carried out using any suitable oxidizing agent/conditions such as, e.g., TEMPO, Dess-Martin periodinane, Swern oxidation to give the furan-3-one. Conversion to the alkynylene moiety may be effected as described for General Procedure 2a, using a suitable Grignard reagent such as an alkynylmagnesium halide, e.g. alkynylmagnesium bromide, such as ethynyl magnesium bromide, or with an organolithium reagent such as an alkynyl lithium reagent, e.g. ethynyl lithium. Selective removal of the 2-protecting group may be carried out under basic conditions using K₂CO₃/MeOH.

In accordance with General Procedure 2c, commercially available diacetone-D-glucose may be used as starting material. The oxidation step may be carried out using any suitable oxidizing agent/conditions such as, e.g., TEMPO, Dess-Martin periodinane or Swern oxidation to give the furan-4-one. Conversion to the alkynylene moiety may be effected as described for General Procedures 2a and 2b, using a suitable Grignard reagent such as an alkynylmagnesium halide, e.g. alkynylmagnesium bromide, such as ethynyl magnesium bromide, or with an organolithium reagent such as an alkynyl lithium reagent, e.g. ethynyl lithium. The 3-hydroxyl group may be protected using any suitable reagent such as 2,5-dichlorobenzyl bromide, 2,4-dichlorobenzyl bromide, allyl halides or silyl halides. Similarly, the hydroxyl groups on the 4-hydroxy and 5-hydroxymethyl substituent may be protected using any suitable reagent such as benzoyl halide, toluoyl halides etc.

General Procedure 2a

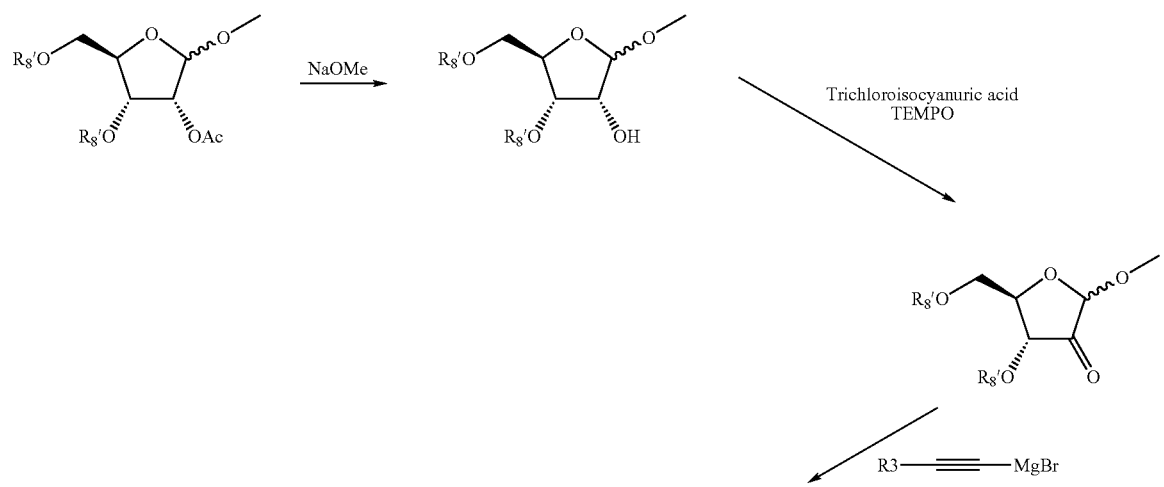

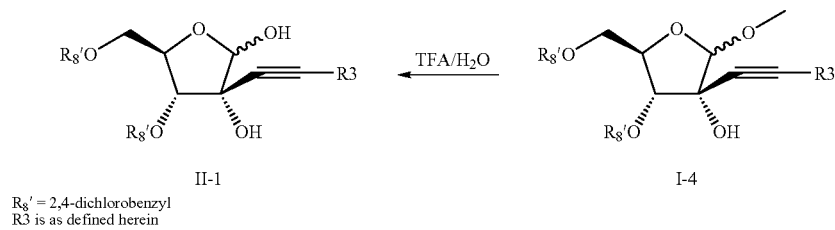

II-1

I-4

$R_8'$ = 2,4-dichlorobenzyl
R3 is as defined herein

General Procedure 2a Step 1: (3R,4S,5R)-5-(2,4-Dichlorobenzyloxymethyl)-4-(2,4-dichlorobenzyloxy)-2-methoxy-tetrahydrofuran-3-ol To (3R,4R,5R)-5-(2,4-dichlorobenzyloxymethyl)-4-(2,4-dichlorobenzyloxy)-2-methoxy-tetrahydrofuran-3-acetate (10 g, 19.1 mmol) in MeOH (150 ml) is added a solution of 30% NaOMe in MeOH (5.37 ml, 28.6 mmol) and the reaction is stirred at 20° C. for 30 mins. The reaction mixture is concentrated and dissolved in IPAC (100 ml), washed with 1 N HCl solution (50 mL) and water (50 mL) and concentrated to give (3R,4S,5R)-5-(2,4-Dichlorobenzyloxymethyl)-4-(2,4-dichlorobenzyloxy)-2-methoxy-tetrahydrofuran-3-ol as a yellowish oil. The obtained crude compound is used for the next step without further purification. $^1$H-NMR (CDCl$_3$, 400 MHz): δ 7.43 (d, J=8.1 Hz, 1H), 7.35-7.31 (m, 3H), 7.23 (dd, J=2.1, 4.0 Hz, 1H), 7.21-7.10 (dd, J=2.1, 4.0 Hz, 1H), 4.92 (d, J=4.6 Hz 1H), 4.77 (d, J=13.4 Hz, 1H), 4.68 (d, J=13.4 Hz, 1H); 4.60 (d, J=13.0 Hz, 1H), 4.56 (d, J=13.0 Hz, 1H), 4.25 (q, J=4.0 Hz, 1H), 4.19 (dd, J=6.8, 4.8 Hz, 1H) 3.86 (dd J=6.9, 7.0 Hz 1H), 3.60 (d, J=10.5 Hz, 2H), 3.48 (s, 3H); $^{13}$C-NMR (CDCl$_3$, 100 MHz): δ 134.2, 134.1, 133.9, 133.5, 133.4, 129.9, 129.8, 129.1, 129.08, 127.11, 127.08, 102.8, 81.6, 77.4, 72.0, 70.8, 70.0, 69.5, 55.6 (one carbon overlapped); ESI-MS: calcd. for C$_{20}$H$_{20}$Cl$_4$O$_5$ (M+NH$_4^+$, 480.0). found: 498.0.

General Procedure 2a Step 2: (4R,5R)-5-(2,4-Dichlorobenzyloxymethyl)-4-(2,4-dichlorobenzyloxy)-2-methoxy-dihydrofuran-3-one To a solution of (3R,4S,5R)-5-(2,4-Dichlorobenzyloxymethyl)-4-(2,4-dichlorobenzyloxy)-2-methoxy-tetrahydrofuran-3-ol (9.20 g, 19.08 mmol) in anhydrous CH$_2$Cl$_2$ (70 mL) and trichloroisocyanuric acid (4.88 g, 21 mmol) in an ice bath is added TEMPO (160 mg, 0.95 mmol). The reaction mixture changes to a yellow suspension and is stirred at 20° C. for 1 h. The reaction is determined to be complete by HPLC and filtered. The solvent is evaporated and toluene (100 mL) is added. The organic phase is washed with sat. NaHCO$_3$ solution (50 mL) and HCl aq. solution (1N, 50 mL). The organic layers are dried (MgSO$_4$), filtered and concentrated to give (4R,5R)-5-(2,4-Dichlorobenzyloxymethyl)-4-(2,4-dichlorobenzyloxy)-2-methoxy-dihydrofuran-3-one as light green oil which is directly used for the next step.

General Procedure 2a Step 3: (3R,4R,5R)-5-(2,4-Dichlorobenzyloxymethyl)-4-(2,4-dichlorobenzyloxy)-3-ethynyl-2-methoxy-tetrahydrofuran-3-ol (I-4)

To a cold (−20° C.) solution of (4R,5R)-5-(2,4-Dichlorobenzyloxymethyl)-4-(2,4-dichlorobenzyloxy)-2-methoxy-dihydrofuran-3-one (9.16 g, 19.07 mmol,) in dry THF (20 mL) is added dropwise a solution of 0.5M alkynylmagnesium bromide (e.g. where R3=H, alkynylmagnesium bromide is ethynylmagnesium bromide) in THF (57.2 mL, 28.6 mmol). The yellow reaction mixture is stirred at the same temperature for 1 h and quenched with saturated NH$_4$Cl (50 ml) and extracted with IPAC (2×70 mL). The organic layer is washed with water (50 mL), concentrated to give (3R,4R, 5R)-5-(2,4-Dichlorobenzyloxymethyl)-4-(2,4-dichlorobenzyloxy)-3-ethynyl-2-methoxy-tetrahydrofuran-3-ol (I-4) (R3=H) as dark red oil which is directly used for the next step.

General Procedure 2a Step 4: (3R,4R,5R)-5-(2,4-Dichlorobenzyloxymethyl)-4-(2,4-dichlorobenzyloxy)-3-ethynyl-tetrahydrofuran-2,3-diol The solution of (3R,4R,5R)-5-(2,4-Dichlorobenzyloxymethyl)-4-(2,4-dichlorobenzyloxy)-3-ethynyl-2-methoxy-tetrahydrofuran-3-ol (I-4) (9.65 g, 19.08 mmol) in TFA and water (30 mL:1.5 mL) is heated to 55° C. The red solution changes to a black solution and is stirred at the same temperature for 24 h. The solvent is evaporated and diluted in DCM (70 mL). The organic layers are washed with sat. Na$_2$CO$_3$ (50 mL), water (50 mL) and concentrated to give a black oil. The crude product is purified by column chromatography (heptane:EA 2:1) to give (3R, 4R,5R)-5-(2,4-Dichlorobenzyloxymethyl)-4-(2,4-dichloro-benzyloxy)-3-ethynyl-tetrahydrofuran-2,3-diol as a red oil (mixture of two anomers). (Ca. 1.4:1 based on NMR analysis and HPLC analysis). ESI-MS: calcd. for C$_{21}$H$_{18}$Cl$_4$O$_5$ (M+NH$_4^+$, 490.0). found: 508.0.

General Procedure 2b

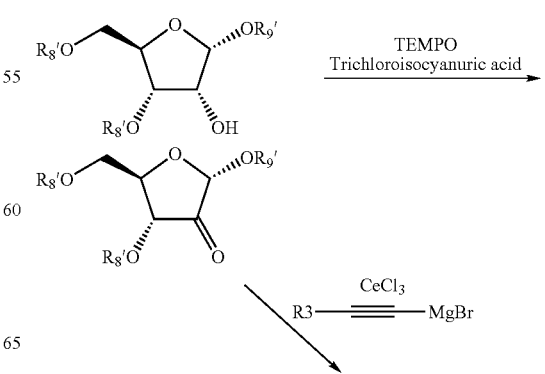

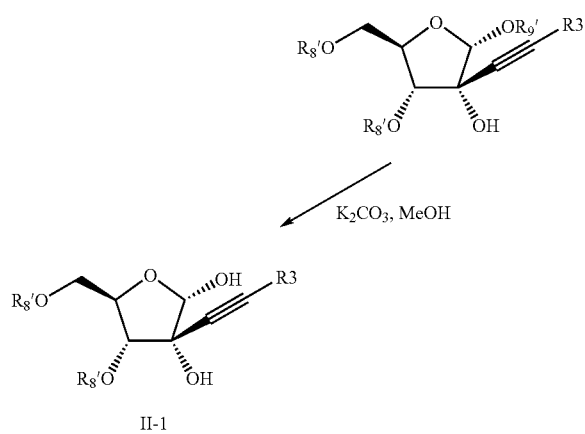

$R_8' = benzoyl$
$R_9' = benzoyl$
$R_3$ is as defined herein

General Procedure 2b Step 1: (2R,3R,4R,5R)-2,4-dibenzoyloxy-5-benzoyloxymethyl-dihydrofuran-3-one 1,3,5-tri-O-benzoyl-α-D-ribofuranose (10.0 g, 21.62 mmol, 1.0 equiv.) is dissolved in dichloromethane (60 ml) and cooled under ice. Trichloroisocyanuric acid (5.52 g, 23.80 mmol, 1.1 equiv.) is added, followed by addition of catalytic amount of TEMPO. The ice bath is removed and the mixture is stirred at room temperature for 1 hour then filtered on Celite®. The organic phase is washed with saturated aqueous $Na_2CO_3$ solution, followed by 1N HCl and brine. The organic layer is dried ($MgSO_4$) and the solvent is evaporated to give (2R,4R,5R)-2,4-dibenzoyloxy-5-benzoyloxymethyl-dihydrofuran-3-one as a white foam. 1H-NMR (400 MHz, CDCl3): δ 8.13-8.01 (m, 6H), 7.65-7.37 (m, 9H), 6.20 (d, 1H, J=1.2 Hz), 5.88 (dd, 1H, J=1.2 Hz, 8.8 Hz), 5.05 (m, 1H, J=1.2 Hz, 4 Hz, 8.8 Hz), 4.84 (dd, 1H, J=4 Hz, 12.4 Hz), 4.65 (dd, 1H, J=4 Hz, 12.4 Hz).

General Procedure 2b Step 2: (2R,3R,4R,5R)-2,4-dibenzoyloxy-5-benzoyloxymethyl-3-ethynyl-tetrahydrofuran-3-ol A dry three-necked flask under $N_2$ is charged with $CeCl_3$ (23.6 g, 95.48 mmol, 4.4 equiv.) and THF (100 ml), which is cooled to −50° C. 1M Ethynylmagnesium bromide (186.8 ml, 93.4 mmol, 4.3 equiv.) is added over 20 min. The suspension is stirred at −50° C. for 1.5 hour. A solution of (2R,4R,5R)-2,4-dibenzoyloxy-5-benzoyloxymethyl-dihydrofuran-3-one (10.0 g, 21.7 mmol, 1.0 equiv.) in THF (80 ml) is added over 10 minutes. After addition, the suspension is stirred at −50° C. for 4 hour. The reaction is quenched with saturated $NH_4Cl$ (200 ml). After being allowed to warm to ambient temperature, the reaction mixture is filtered and extracted with $CH_2Cl_2$ (200 ml×3). The organic phase is dried over anhydrous $Na_2SO_4$, and concentrated to give a foam (2R, 3R,4R, 5R)-2,4-dibenzoyloxy-5-benzoyloxymethyl-3-ethynyl-tetrahydrofuran-3-ol. 1H-NMR (400 MHz, CDCl3): δ 8.05-8.01 (m, 6H), 7.65-7.37 (m, 9H), 6.59 (s, 1H), 5.53 (d, 1H, J=2.8 Hz), 4.80-4.77 (m, 1H), 4.70 (dd, 1H, J=5.2 Hz, 12 Hz), 4.65 (dd, 1H, J=6 Hz, 12 Hz), 3.02 (bs, 1H), 2.65 (s, 1H).

Alternatively, the same procedure as that described in step 2 can be used, except that the reaction temperature is −30° C. and the reaction time is 3 hours, using (2R,4R,5R)-2,4-dibenzoyloxy-5-benzoyloxymethyl-dihydrofuran-3-one (1.0 g, 2.17 mmol, 1.0 equiv.), 1M ethynylmagnesium bromide (13 ml, 6.51 mmol, 3 equiv.) $CeCl_3$ (1.77 g, 7.16 mmol, 3.3 equiv.) and THF (18 ml), to give (2R,3R,4R,5R)-2,4-dibenzoyloxy-5-benzoyloxymethyl-3-ethynyl-tetrahydrofuran-3-ol.

General Procedure 2b Step 3: (2R,3R,4R,5R)-4-benzoyloxy-5-benzoyloxymethyl-3-ethynyl-tetrahydrofuran-2,3-diol Intermediate (2R,3R,4R,5R)-2,4-dibenzoyloxy-5-benzoyloxymethyl-3-ethynyl-tetrahydro-furan-3-ol (2.048 g, 4.21 mmol, 1.0 equiv.) is dissolved in methanol (10 ml) and THF (10 ml). $K_2CO_3$ (176 mg, 1.26 mmol, 0.3 equiv.) is added, The reaction is stirred at ambient temperature for 2 h, filtered on silica gel, concentrated and purified by flash chromatography to give (2R,3R,4R,5R)-4-benzoyloxy-5-benzoyloxymethyl-3-ethynyl-tetrahydrofuran-2,3-diol as a foam. 1H-NMR (400 MHz, $CDCl_3$): δ 8.06-7.96 (m, 4H), 7.54-7.26 (m, 6H), 5.88 (d, 0.26H, J=6.4 Hz), 5.54 (s, 0.72H), 5.53 (d, 0.72H, J=5.2 Hz), 5.41 (s, 0.28H), 5.28 (bs, 1H), 4.67-4.49 (m, 3H), 4.22 (bs, 1H), 2.67 (s, 0.26H), 2.59 (s, 0.71H); 13C-NMR (100 MHz, CDCl3): δ 166.74, 166.61, 165.74, 165.66, 133.79, 133.71, 133.52, 133.33, 133.24, 130.11, 130.05, 130.02, 129.89, 129.81, 129.44, 129.41, 128.86, 128.75, 128.57, 128.41, 128.36, 81.87, 80.07, 79.23, 77.89, 77.21, 76.61, 76.39, 75.77, 75.58, 72.83, 65.29, 64.26.

General Procedure 2c

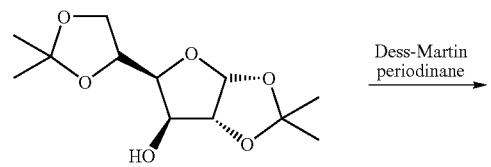

-continued

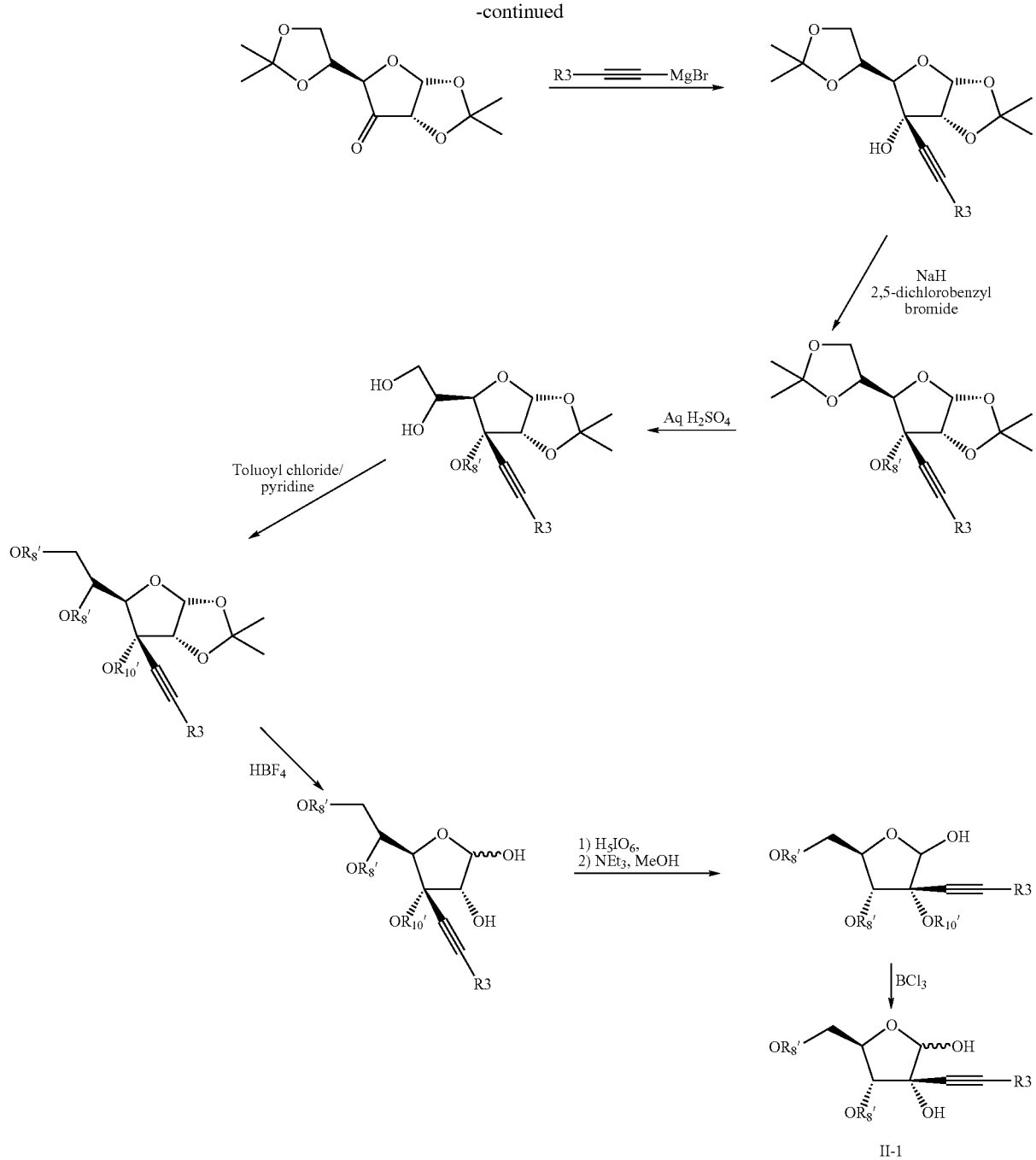

R$_8'$ = benzoyl or toluoyl
R$_{10}'$ = 2,4-dichlorobenzyl or 2,5-dichlorobenzyl
R3 is as defined herein General Procedure 2c Step 1: 1,2:5,6-Di-O-isopropylidene-α-D-ribohexofuran-3-ulose Diacetone-D-glucose (2.0 g, 6.9 mmol) is dissolved in CH$_2$Cl$_2$ (40 ml). Dess-Martin periodinane (7.5 g, 13.8 mmol, 2.0 equiv.) is added and the reaction is stirred at room temperature overnight. Then 10% Na$_2$S$_2$O$_3$ solution (20 ml) and saturated NaHCO$_3$ solution (20 ml) are added and the reaction is stirred for 15 mins until the organic layer changes to a clear solution. Another 40 ml CH$_2$Cl$_2$ are added and the CH$_2$Cl$_2$ layer is separated, washed with NaHCO$_3$ solution (20 ml), brine (20 ml), dried (Na$_2$SO$_4$), filtered and concentrated to yield the crude intermediate 1,2:5,6-Di-O-isopropylidene-a-D-ribohexofuran-3-ulose. The crude intermediate 1,2:5,6-Di-O-isopropylidene-a-D-ribohexofuran-3-ulose is azeotropic distilled with toluene (2×25 ml), dissolved in toluene (20 ml) and used in the next step.

General Procedure 2c Step 2: 1,2:5,6-Di-O-isopropylidene-3-C-ethynyl-α-D-allofuranose Intermediate 1,2:5,6-Di-O-isopropylidene-a-D-ribohexofuran-3-ulose (1.82 g, 6.9 mmol, 1 equiv.) in toluene (20 ml)

is cooled to 0° C., then 0.5 M ethyne MgBr in THF solution (55.2 ml, 27.6 mmol, 4 equiv.) is added and the mixture is stirred under room temperature for 1 h. The reaction is quenched with 10% NH$_4$Cl solution (40 ml) and the crude product is partitioned between ethyl acetate (100 ml) and the aqueous phase. The aqueous phase is further extracted with ethyl acetate (3×20 ml) and the combined ethyl acetate is washed with brine (40 ml), dried (Na$_2$SO$_4$), filtered and concentrated to dry to give crude intermediate 1,2:5,6-Di-O-isopropylidene-3-C-ethynyl-α-D-allofuranose as a yellowish foam.

General Procedure 2c Step 3: 3-C-ethynyl-1,2:5,6-bis-O-(1-methylethylidene)-3-O-(2,5-dichorobenzyl)-α-D-allofuranose Intermediate 1,2:5,6-Di-O-isopropylidene-3-C-ethynyl-α-D-allofuranose (2.84 g, 10 mmol) is dissolved in DMF (15 ml) and cooled under ice. NaH (600 mg as 60% dispersion in oil, 15 mmol, 1.5 equiv.) is added and the reaction is stirred for 2 mins, then 2,5-dichlorobenzyl bromide (3.6 g, 15 mmol, 1.5 equiv.) is added and the mixture is stirred at room temperature for 3 h. Ethyl acetate (120 ml) is added and washed with 1N HCl (3×25 ml), brine (2×25 ml), dried (Na$_2$SO$_4$), filtered and concentrated to dry to yield the crude intermediate 3-C-ethynyl-1,2:5,6-bis-O-(1-methylethylidene)-3-O-(2,5-dichlorobenzyl)-α-D-allofuranose as pale yellow oil.

General Procedure 2c Step 4: 3-C-ethynyl-1,2-O-(1-methylethylidene)-3-O-(2,5-dichlorobenzyl)-α-D-allofuranose Crude Intermediate 3-C-ethynyl-1,2:5,6-bis-O-(1-methylethylidene)-3-O-(2,5-dichlorobenzyl)-α-D-allofuranose (5.91 g, 10 mmol) is dissolved in acetonitrile (50 ml). 5 vol % H$_2$SO$_4$ solution (12 ml) is added and the mixture is stirred at room temperature overnight. NaOAc solution (0.1 M, 20 ml) is added and the mixture is evaporated under vacuum. To the solution residue is added ethyl acetate (120 ml). The ethyl acetate layer is washed with saturated NaHCO$_3$ solution (2×25 ml), brine (2×25 ml), dried (Na2SO4), filtered and concentrated to yield the crude intermediate 3-C-ethynyl-1,2-O-(1-methylethylidene)-3-O-(2,5-dichlorobenzyl)-α-D-allofuranose.

General Procedure 2c Step 5: 3-C-ethynyl-1,2-O-(1-methylethylidene)-3-O-(2,5-dichlorobenzyl)-5,6-bis(4-methylbenzoate)-α-D-allofuranose-dibenzoate Crude intermediate 3-C-ethynyl-1,2-O-(1-methylethylidene)-3-O-(2,5-dichlorobenzyl)-α-D-allofuranose. (5.6 g, 10 mmol) is dissolved in acetonitrile (30 ml). Pyridine (7.9 ml, 100 mmol, 10 equiv.) is added, followed by p-toluoyl chloride (3.11 ml, 30 mmol, 3 equiv.). The reaction is stirred at 55° C. for 3 h and concentrated under vacuum. Ethyl acetate (120 ml) is added and washed with 1N HCl solution (3×25 ml), brine (2×25 ml), dried (Na$_2$SO$_4$), filtered, and concentrated to dry to yield the crude intermediate 3-C-ethynyl-1,2-O-(1-methylethylidene)-3-O-(2,5-dichlorobenzyl)-5,6-bis(4-methylbenzoate)-α-D-allofuranose as an oil.

General Procedure 2c Step 6: 3-C-ethynyl-3-O-(2,5-dichlorobenzyl)-5,6-bis(4-methylbenzoate)-D-allose Crude intermediate 3-C-ethynyl-1,2-O-(1-methylethylidene)-3-O-(2,5-dichlorobenzyl)-bis(4-methylbenzoate)-α-D-allofuranose (7.4 g, 10 mmol) is dissolved in acetonitrile (35 ml), 50% HBF$_4$ in H$_2$O solution (6.3 ml, 50 mmol, 5 equiv.) diluted with 7 ml H$_2$O is added. The reaction mixture is stirred at 60° C. for 3 h. Ethyl acetate (200 ml) is added to the reaction mixture and washed with saturated NaHCO$_3$ solution (2×30 ml), 1 N HCl solution (2×30 ml), brine (2×30 ml), dried (Na$_2$SO$_4$), filtered, concentrated and purified by flash chromatography (Hexane:Ethyl acetate=70:30) to yield 3-C-ethynyl-3-O-(2,5-dichlorobenzyl)-5,6-bis(4-methylbenzoate)-D-allose as a white foam (4.41 g, 7.36 mmol, 73.6% over 4 steps). 1H-NMR (CDCl$_3$): δ 7.92-7.80 (m, 4H), 7.38 (d, 0.79H, J=2.4 Hz), 7.34 (d, 0.23H, J=2.1 Hz), 7.30-7.09 (m, 6H), 5.84-5.60 (m, 1H), 5.51 (d, 0.76H, J=3.9 Hz), 5.40 (d, 0.22H, J=1.5 Hz), 4.94-4.50 (m, 5H), 4.29 (d, 1H, J=4.2 Hz), 2.87 (s, 0.23H), 2.80 (s, 0.76H), 2.34 (s, 6H). 13C-NMR (CDCl$_3$): δ 166.71, 166.59, 165.66, 165.63, 144.08, 143.88, 136.59, 136.41, 133.01, 132.98, 131.59, 131.25, 130.61, 130.48, 129.97, 129.91, 129.75, 129.45, 129.30, 129.26, 129.22, 127.16, 127.06, 102.76, 96.78, 81.53, 81.25, 80.91, 80.83, 80.67, 80.55, 80.21, 77.83, 77.74, 76.81, 76.70, 72.10, 71.24, 65.67, 65.61, 64.07, 63.84, 21.80, 21.78.

General Procedure 2c Step 7: 2-C-ethynyl-2-O-(2,5-dichlorobenzyl)-3,5-bis(4-methylbenzoate)-D-ribose Intermediate 3-C-ethynyl-3-O-(2,5-dichlorobenzyl)-5,6-bis(4-methylbenzoate)-D-allose (2.20 g, 3.67 mmol) is dissolved in acetonitrile (20 ml) and cooled to 0° C. A solution of periodic acid (1.25 g, 5.50 mmol, 1.5 equiv.) in H$_2$O (5.0 ml) is added and the reaction is stirred for 30 mins. Isopropyl acetate (50 ml) is added and washed with saturated NaHCO$_3$ solution (50 ml), 5% sodium thiosulfate in water solution (30 ml). brine (30 ml), dried (Na$_2$SO$_4$), filtered and concentrated to dry. MeOH (20 ml) is added to the oil residue and cooled to 0° C. Triethylamine (1.09 ml, 7.84 mmol, 2.1 equiv.) is added and the reaction is stirred at 4° C. for 60 h. Ethyl acetate (200 ml) is added and the organic phase is washed with 1 N HCl solution (2×40 ml), brine (2×30 ml), dried (Na$_2$SO$_4$), filtered, concentrated and purified by flash chromatography (Hexane:Ethyl acetate=75:25) to yield the title compound as a yellowish paste. 1H-NMR (CDCl$_3$): δ 7.99-7.84 (m, 4H), 7.51 (d, 0.53H, J=2.4 Hz), 7.33 (d, 0.43H, J=2.4 Hz), 7.28-7.10 (m, 6H), 5.94 (d, 0.53H, J=5.7 Hz), 5.73 (d, 0.43H, J=4.2 Hz), 5.57 (s, 0.45H), 5.46 (s, 0.53H), 4.98-4.85 (m, 2H), 4.80-4.54 (m, 3H), 2.81 (s, 0.48H), 2.80 (s, 0.40H), 2.44-2.34 (m, 6H). 13C-NMR (CDCl$_3$): δ 166.65, 166.47, 165.62, 165.44, 144.89, 144.73, 144.07, 144.05, 137.64, 136.75, 133.04, 130.82, 130.46, 130.24, 130.21, 130.10, 130.06, 129.60, 129.51, 129.29, 129.26, 129.06, 128.94, 128.60, 128.39, 127.14, 127.12, 126.31, 126.13, 100.36, 100.34, 81.54, 80.24, 80.07, 79.51, 78.64, 78.48, 76.89, 76.60, 76.45, 66.34, 65.38, 64.76, 64.25, 21.95, 21.88.

General Procedure 2c Step 8: (3R,4R,5R)-4-(4-methylbenzoyloxy)-5-(4-methylbenzoyloxymethyl)-3-ethynyl-tetrahydro-furan-2,3-diol Intermediate 2-C-ethynyl-2-O-(2,5-dichlorobenzyl)-3,5-bis(4-methylbenzoate)-D-ribose (1.113 g, 1.95 mmol) is dissolved in CH$_2$Cl$_2$ (30 ml) and cooled to −35° C. (o-xylene and dry ice, with acetonitrile added). 1 M BCl$_3$ in CH$_2$Cl$_2$ solution (15.6 ml, 15.6 mmol, 8 equiv.) is added and the mixture is stirred at −35° C. for 3 h. Cold methanol (10 ml) is added to the reaction, followed by KHCO$_3$ powder (3.9 g, 39.0 mmol, 20 equiv.). After stirring for 10 mins, the mixture is filtered. CH$_2$Cl$_2$ (30 ml) and 1N HCl solution (20 ml) are added and the two layers are partitioned. The aqueous layer is further extracted with CH$_2$Cl$_2$ (20 ml). The combined CH$_2$Cl$_2$ solution is washed with brine (15 ml), dried (Na$_2$SO$_4$), filtered, concentrated and purified by flash chromatography (Hexane: Ethyl acetate=70:30) to yield (3R,4R,5R)-4-(4-methylbenzoyloxyl)-5-(4-methylbenzoyloxymethyl)-3-ethynyl-tetrahydrofuran-2,3-diol as a white foam. Starting material can be recovered. 1H-NMR (CDCl$_3$): δ 7.96-7.84 (m, 4H), 7.28-7.10 (m, 4H), 5.80-5.30 (m, 2H), 4.70-4.45 (m, 3H), 2.67 (s, 0.16H), 2.59 (s, 0.63H), 2.44-2.34 (m, 6H). 13C-NMR (CDCl$_3$): δ 166.80, 166.61, 165.79, 165.67, 144.93, 144.78, 144.10, 144.07, 130.20, 130.08, 130.02, 129.50, 129.47, 129.26, 129.22, 127.02, 126.27, 101.73, 100.18, 81.85, 80.07, 79.57, 78.47, 76.75, 76.50, 76.13, 75.63, 73.07, 65.10, 64.16, 21.91, 21.84.

General Procedure 3: Preparation of the Compounds of the Invention from the Intermediate Diprotected (at the 4-hydroxyl and 5-hydroxymethyl substituents): (3R,4R, 5R)-3-alkynyl-5-hydroxymethyl-tetrahydrofuran-2,3,4-triol (II-1)

Compound II-1 may be converted to the epoxide using any suitable sulfonyl chloride such as Ms-Cl or Ts-Cl, or sulfonic acid anhydride such as Ms-O-Ms or Ts-O-Ts. The epoxide is coupled to a suitable base or base analog, to give the nucleoside analog. Although General Procedure 3 describes the base analog 4-chloro-7H-pyrrolo[2,3-d]pyrimidine, it will be appreciated that any suitable base moiety can be used, such as, for example an adenine or guanine analog, where X=N, CH or CR4, R1'=halogen, NR5R6 or OR7, R2'=H, halogen or NR5R6 and R3, R4, R5, R6 and R7 are as defined herein. In some examples, X may be CH. In other examples X may be CR4. In some examples R4 may be halogen, e.g. F or I. In other examples R4 may be alkynyl, e.g. ethynyl. In some examples R1' may be halogen, e.g. Cl. In other examples, R1' may be amino or alkoxy, e.g. methoxy. In some examples R2' may be H. Other examples of bases/base analogs include, e.g., 4-chloro-7H-pyrrolo[2,3-d]pyrimidine, 4-chloro-5-fluoro-pyrrolo[2,3-d]pyrimidine, 4-chloro-5-iodo-pyrrolo[2,3-d]pyrimidine, 7H-pyrrolo[2,3-d]pyrimidin-4-yl-isoindole-1,3-dione and 4-chloro-5-acetylene-pyrrolo[2,3-d]pyrimidine. The coupling step may be carried out using any suitable reagent such as a suitable base, e.g. NaH. The protecting groups R8' may be any suitable protecting group, e.g. 2,4-dichlorobenzyl, or, 2,5-dichlorobenzyl, toluoyl, benzoyl or benzyl. These may be removed by suitable reagents e.g. using BCl$_3$ or a suitable base, e.g. sodium methoxide.

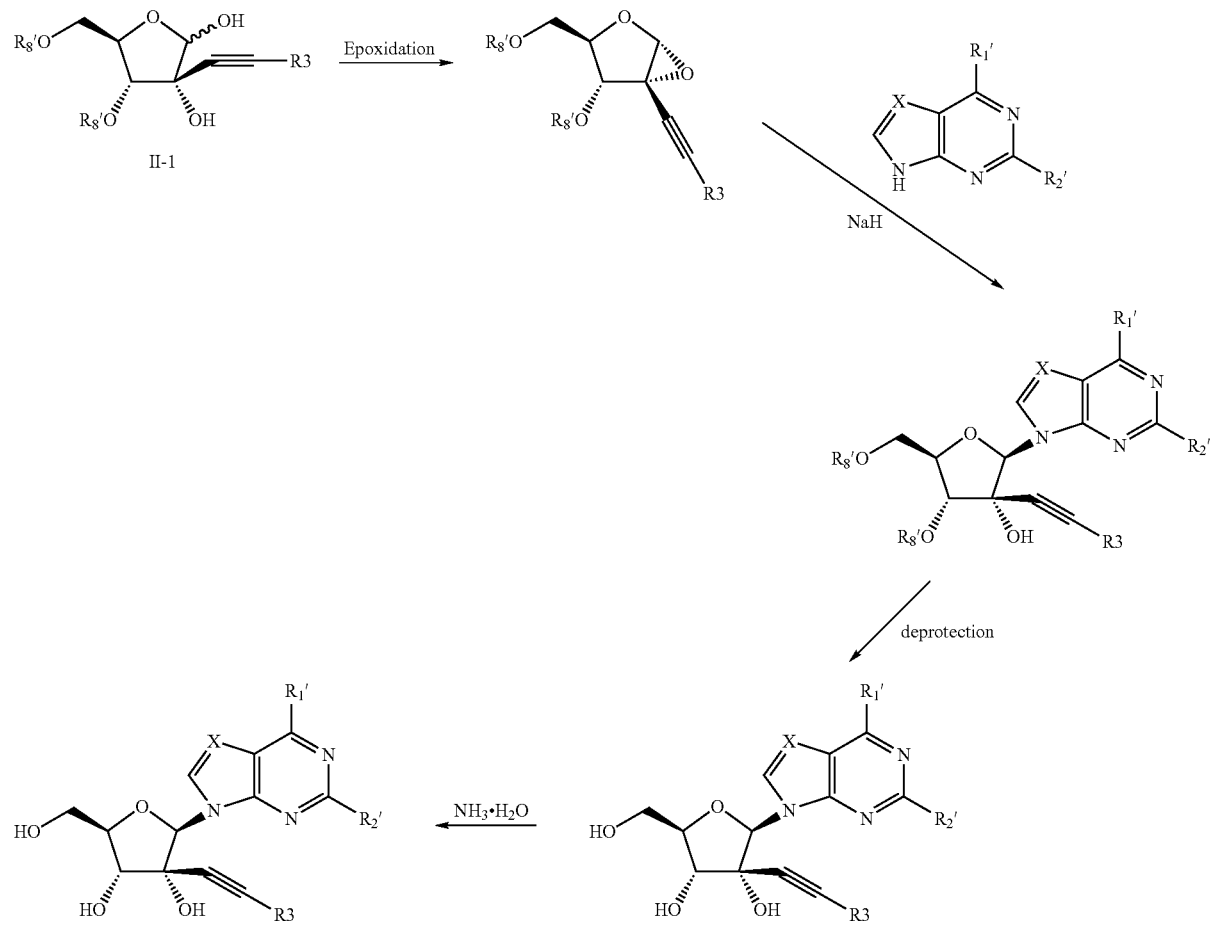

R$_8$' = 2,4-dichlorobenzyl, toluoyl, benzoyl or benzyl
X = N, CH or CR4
R$_1$' = halogen, NR5R6 or OR7
R$_2$' = H, halogen or NR5R6
R3, R4, R5, R6 and R7 are as defined herein

General Procedure 3 Step 1: 1,2-anhydro-2-C-ethynyl-3,5-bis(4-methylbenzoyl)-α-D-ribofuranose Intermediate (3R,4R,5R)-4-(4-methylbenzoyloxyl)-5-(4-methylbenzoyloxymethyl)-3-ethynyl-tetrahydro-furan-2,3-diol (II-1) (304 mg, 0.74 mmol) is dissolved in CH$_2$Cl$_2$ (4 ml). Triethylamine (308.4 μL, 2.22 mmol, 3 equiv.) is added and the mixture is heated to 30° C. A solution of methanesulfonyl anhydride (167.6 mg, 0.96 mmol, 1.3 equiv.) in CH$_2$Cl$_2$ (1 ml) is added drop-wise over 10 mins. The reaction is stirred at 40° C. for 2.5 h and CH$_2$Cl$_2$ (50 ml) is added. The CH$_2$Cl$_2$ solution is washed with H$_2$O (2×5 ml), brine (10 ml), dried (Na$_2$SO$_4$), filtered, and concentrated to dry to yield the crude intermediate 1,2-anhydro-2-C-ethynyl-3,5-bis(4-methylbenzoyl)-α-D-Ribofuranose.

General Procedure 3 Step 2: (2R,3R,4R,5R)-2-(4-Chloro-pyrrolo[2,3-d]pyrimidin-7-yl)-4-(4-methylbenzoyloxy)-5-(4-methylbenzoyloxymethyl)-3-ethynyl-tetrahydrofuran-3-ol To a dry flask charged with 4-chloro-7H-pyrrolo[2,3-d]pyrimidine (227.3 mg, 1.48 mmol, 2 equiv.) are added NaH (59.2 mg as 60% dispersion in oil, 1.48 mmol, 2 equiv.) and acetonitrile (4 ml), stirring for 10 mins. Crude intermediate 1,2-anhydro-2-C-ethynyl-3,5-bis(4-methylbenzoyl)-α-D-ribofuranose (383 mg, 0.74 mmol, 1 equiv.) dissolved in acetonitrile (2 ml) is added and the reaction is heated at 50° C. for 15 h. The mixture is neutralized to pH 7.0 by addition of 1N HCl solution and evaporated under vacuum. Ethyl acetate (50 ml) is added to the residue solution and it is washed with 1 N HCl solution (8 ml), H$_2$O (8 ml), brine (10 ml), dried (Na$_2$SO$_4$), filtered, and concentrated to dry to yield the crude intermediate (2R,3R,4R,5R)-2-(4-Chloro-pyrrolo[2,3-d]pyrimidin-7-yl)-4-(4-methylbenzoyloxy)-5-(4-methylbenzoyloxymethyl)-3-ethynyl-tetrahydro-furan-3-ol (434 mg).

General Procedure 3 Step 3: (2R,3R,4R,5R)-2-(4-Chloro-pyrrolo[2,3-d]pyrimidin-7-yl)-3-ethynyl-5-hydroxymethyl-tetrahydrofuran-3,4-diol Crude intermediate (2R,3R,4R,5R)-2-(4-Chloro-pyrrolo[2,3-d]pyrimidin-7-yl)-4-(4-methylbenzoyloxy)-5-(4-methylbenzoyloxymethyl)-3-ethynyl-tetrahydro-furan-3-ol (434 mg, 0.74 mmol) is dissolved in MeOH (5 ml) and CH$_2$Cl$_2$ (5 ml). 30% sodium methoxide in methanol solution (1.38 ml, 7.4 mmol, 10 equiv.) is added and the mixture is stirred at room temperature for 15 mins. The mixture is neutralized to pH 7.0 by addition of 1N HCl solution and evaporated under vacuum to dry, purified by flash chromatography (CH$_2$Cl$_2$:MeOH=92:8) to yield (2R,3R,4R,5R)-2-(4-Chloro-pyrrolo[2,3-d]pyrimidin-7-yl)-3-ethynyl-5-hydroxymethyl-tetrahydrofuran-3,4-diol. 1H-NMR (CDCl$_3$): δ 8.58 (s, 1H), 8.00 (d, 1H, J=3.9 Hz), 6.68 (d, 1H, J=3.9 Hz), 6.49 (s, 1H), 4.51 (d, 1H, J=9.0 Hz), 4.20-3.75 (m, 3H), 2.51 (s, 1H). ESI-MS: calcd. for C13H12ClN3O4 (309.05). found: 310.3.

General Procedure 3 Step 4: (2R,3R,4R,5R)-2-(4-Amino-pyrrolo[2,3-d]pyrimidin-7-yl)-3-ethynyl-5-hydroxymethyl-tetrahydrofuran-3,4-diol A mixture of (2R,3R,4R,5R)-2-(4-Chloro-pyrrolo[2,3-d]pyrimidin-7-yl)-3-ethynyl-5-hydroxymethyl-tetrahydrofuran-3,4-diol (198.0 mg, 0.64 mmol,) and NH$_3$.H$_2$O (30 mL) in a glass pressure tube is heated at 100° C. for 5 h. The reaction mixture is concentrated to dry and purified by flash chromatography (CH$_2$Cl$_2$:MeOH=80:20) to yield (2R,3R,4R,5R)-2-(4-Amino-pyrrolo[2,3-d]pyrimidin-7-yl)-3-ethynyl-5-hydroxymethyl-tetrahydrofuran-3,4-diol as pale yellow solid. 1H NMR (300 MHz, MeOD): δ 8.07 (1H, s), 7.48 (1H, d, J=3.9 Hz), 6.58 (1H, d, J=3.6 Hz), 6.29 (1H, s), 4.49 (1H, d, J=8.4 Hz), 4.08-3.96 (2H, m), 3.90-3.75 (1H, m), 2.52 (1H, s). 1H NMR (300 MHz, DMSO-d6): δ 8.05 (1H, s), 7.41 (1H, d, J=3.6 Hz), 6.97 (2H, s), 6.55 (1H, d, J=3.6 Hz), 6.23 (1H, s), 6.16 (1H, s), 5.61 (1H, d, J=7.5 Hz), 5.13 (1H, t, J=4.9 Hz), 4.33 (1H, t, J=7.8 Hz), 3.90-3.70 (2H, m), 3.78-3.68 (1H, m), 3.01 (1H, s). 13C NMR (75 MHz, DMSO-d6): δ 157.4, 151.6, 150.1, 121.6, 102.4, 99.6, 89.6, 82.1, 81.8, 76.5, 75.8, 74.0, 59.7. ESI-MS: calcd. for C13H14N4O4 (290.1). found: 291.2.

EXAMPLES

The invention is described with reference to the following examples. It is to be appreciated that the invention is not limited to these examples.

ABBREVIATIONS

DMSO dimethylsulfoxide
THF tetrahydrofuran
DMAP 4-dimethylaminopyridine
NMR nuclear magnetic resonance
TEA triethylamine
MS mass spectroscopy
DMF dimethylformamide
DCM dichloromethane
PBS phosphate buffered saline
FBS fetal bovine serum
HRP horse radish peroxidase
TMB 3,3',5,5'-tetramethylbenzidine
DMEM Dulbecco's Modified Eagle's Medium

I. Preparation of Compounds of the Invention

Example 1

(2R,3R,4R,5R)-2-(4-Amino-pyrrolo[2,3-d]pyrimidin-7-yl)-3-ethynyl-5-hydroxymethyl-tetrahydrofuran-3,4-diol

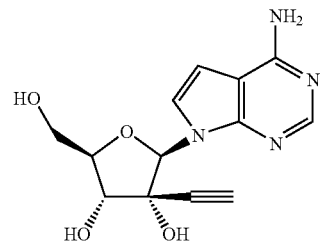

The title compound is prepared from commercially available (3R,4R,5R)-5-(2,4-dichlorobenzyloxymethyl)-4-(2,4-dichlorobenzyloxy)-2-methoxy-tetrahydrofuran-3-acetate I-1 and 4-chloropyrrolo[2,3-d]pyrimidine according to General Procedure 1.

Alternatively, the compound is prepared according to General Procedure 2a, 2b or 2c and General Procedure 3.

Yellow solid. 1H NMR (300 MHz, MeOD): δ 8.07 (1H, s), 7.48 (1H, d, J=3.9 Hz), 6.58 (1H, d, J=3.6 Hz), 6.29 (1H, s), 4.49 (1H, d, J=8.4 Hz), 4.08-3.96 (2H, m), 3.90-3.75 (1H, m), 2.52 (1H, s). 1H NMR (300 MHz, DMSO-d6): δ 8.05 (1H, s), 7.41 (1H, d, J=3.6 Hz), 6.97 (2H, s), 6.55 (1H, d, J=3.6 Hz), 6.23 (1H, s), 6.16 (1H, s), 5.61 (1H, d, J=7.5 Hz), 5.13 (1H, t, J=4.9 Hz), 4.33 (1H, t, J=7.8 Hz), 3.90-3.70 (2H, m), 3.78-3.68 (1H, m), 3.01 (1H, s). 13C NMR (75 MHz, DMSO-d6): δ 157.4, 151.6, 150.1, 121.6, 102.4, 99.6, 89.6, 82.1, 81.8, 76.5, 75.8, 74.0, 59.7. ESI-MS: calcd. for C13H14N4O4 (290.1). found: 291.2 (M+1).

$[\alpha]_D$: +160.0° (ATAGO AP-100 polarimeter; methanol solvent; 100 mm observation tube; 23.4° C.; wavelength 589 nm).

Example 2

(2R,3R,4R,5R)-2-(4-Chloro-pyrrolo[2,3-d]pyrimidin-7-yl)-3-ethynyl-5-hydroxymethyl-tetrahydrofuran-3,4-diol

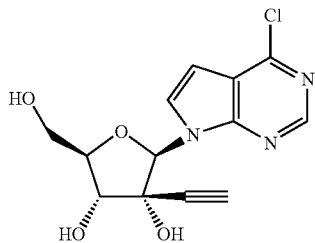

The title compound is prepared from commercially available (3R,4R,5R)-5-(2,4-dichlorobenzyloxymethyl)-4-(2,4-dichlorobenzyloxy)-2-methoxy-tetrahydrofuran-3-acetate I-1 and 4-chloropyrrolo[2,3-d]pyrimidine according to General Procedure 1.

Alternatively, the compound is prepared according to General Procedure 2a, 2b or 2c and General Procedure 3.

White solid. 1H-NMR (300 MHz, MeOH-d4): δ 8.59 (1H, s), 8.01 (1H, d, J=4.2 Hz), 6.69 (1H, d, J=3.9 Hz), 6.49 (1H, s), 4.50 (1H, d, J=9.3 Hz), 4.06-3.99 (2H, m), 3.87-3.82 (1H, m), 2.52 (1H, s). ESI-MS: calcd. for C13H12ClN3O4 (309.2). found: 310.6 (M+1).

Example 3

(2R,3R,4R,5R)-2-(4-Chloro-5-fluoro-pyrrolo[2,3-d]pyrimidin-7-yl)-3-ethynyl-5-hydroxymethyl-tetrahydrofuran-3,4-diol

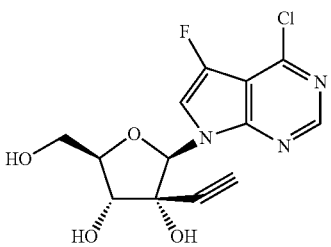

The title compound is prepared from commercially available (3R,4R,5R)-5-(2,4-dichlorobenzyloxymethyl)-4-(2,4-dichlorobenzyloxy)-2-methoxy-tetrahydrofuran-3-acetate I-1 and 4-chloro-5-fluoro-pyrrolo[2,3-d]pyrimidine according to General Procedure 2a or 2b and General Procedure 3.

1H NMR (300 MHz, MeOD): δ 8.60 (1H, s), 7.92 (1H, d, J=2.1 Hz), 6.54 (1H, d, J=2.1 Hz), 4.46 (1H, d, J=8.7 Hz), 4.05-3.95 (2H, m), 3.90-3.80 (1H, m), 2.56 (1H, s). ESI-MS: calcd. for C13H11ClFN3O4 (327.0). found: 328.2.

Example 4

(2R,3R,4R,5R)-2-(4-Amino-5-fluoro-pyrrolo[2,3-d]pyrimidin-7-yl)-3-ethynyl-5-hydroxymethyl-tetrahydrofuran-3,4-diol

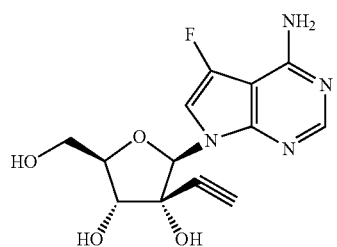

The title compound is prepared from commercially available (3R,4R,5R)-5-(2,4-dichloro-benzyloxymethyl)-4-(2,4-dichlorobenzyloxy)-2-methoxy-tetrahydrofuran-3-acetate I-1 and 4-chloro-5-fluoro-pyrrolo[2,3-d]pyrimidine according to General Procedure 2a or 2c and General Procedure 3.

1H NMR (300 MHz, MeOD): δ 8.08 (1H, s), 7.39 (1H, d, J=2.1 Hz), 6.34 (1H, d, J=2.1 Hz), 4.44 (1H, d, J=9.0 Hz), 4.05-3.95 (2H, m), 3.85-3.75 (1H, m), 2.58 (1H, s). ESI-MS: calcd. for C13H13FN4O4 (308.1). found: 309.2.

Example 5

(2R,3R,4R,5R)-2-(4-Chloro-5-iodo-pyrrolo[2,3-d]pyrimidin-7-yl)-3-ethynyl-5-hydroxymethyl-tetrahydrofuran-3,4-diol

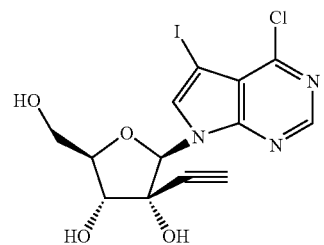

The title compound is prepared from commercially available (3R,4R,5R)-5-(2,4-dichlorobenzyloxymethyl)-4-(2,4-dichlorobenzyloxy)-2-methoxy-tetrahydrofuran-3-acetate I-1 and 4-chloro-5-iodo-pyrrolo[2,3-d]pyrimidine according to General Procedure 1.

Alternatively, the compound is prepared according to General Procedure 2a and General Procedure 3.

White solid. $^1$H-NMR (300 MHz, DMSO-d$_6$): δ 8.69 (1H, s), 8.36 (1H, s), 6.39 (1H, s), 6.33 (1H, s), 5.70 (1H, d, J=7.60 Hz), 5.33 (1H, t, J=4.85 Hz), 4.34 (dd, J=8.94, 7.47 Hz, 1H), 3.92-3.81 (2H, m), 3.71-3.64 (1H, m), 3.04 (1H, s).

ESI-MS: calcd. for C13H11ClIN3O4 (435.6). found: 436.1.2 (M+1).

$^{13}$C NMR (75 MHz, DMSO-d$_6$): δ 151.67, 151.32, 144.28, 133.96, 117.00, 90.85, 83.06, 82.08, 77.46, 76.61, 73.85, 59.54, 53.76.

Example 6

(2R,3R,4R,5R)-3-Ethynyl-5-hydroxymethyl-2-(5-iodo-4-methoxy-pyrrolo[2,3-d]pyrimidin-7-yl)-tetrahydrofuran-3,4-diol

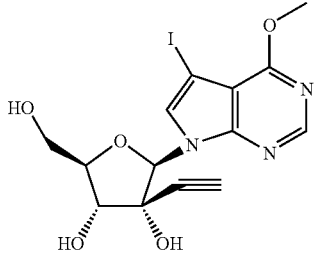

The title compound is prepared from commercially available (3R,4R,5R)-5-(2,4-dichlorobenzyloxymethyl)-4-(2,4-dichlorobenzyloxy)-2-methoxy-tetrahydrofuran-3-acetate I-1 and 4-chloro-5-iodo-pyrrolo[2,3-d]pyrimidine according to General Procedure 1, followed by conversion of the chloro compound to the methoxy compound by treatment with methanol.

Alternatively, the compound is prepared according to General Procedure 2a and General Procedure 3.

White solid. $^1$H-NMR (300 MHz, DMSO-d$_6$): δ 8.44 (1H, s), 7.97 (1H, s), 6.28 (2H, s), 5.66 (1H, d, J=7.34 Hz), 5.24 (1H, t, J=4.73 Hz), 4.33 (t, J=7.76, Hz, 1H), 4.05 (3H, s), 3.88-3.79 (2H, m), 3.67-3.62 (1H, m), 3.03 (1H, s). ESI-MS: calcd. for C$_{14}$H$_{14}$IN$_3$O$_5$ (431.2). found: 432.1.2 (M+1).

$^{13}$C NMR (75 MHz, DMSO-d$_6$): δ 162.82, 152.19, 144.62, 144.54, 144.41, 129.81, 107.02, 82.79, 82.26, 76.58, 73.98, 59.68, 54.37, 51.69.

Example 7

(2R,3R,4R,5R)-2-(4-Amino-5-iodo-pyrrolo[2,3-d]pyrimidin-7-yl)-3-ethynyl-5-hydroxymethyl-tetrahydrofuran-3,4-diol

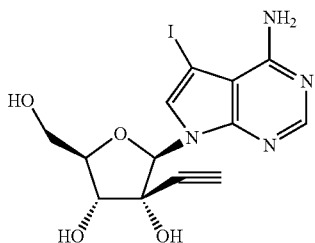

The title compound is prepared from commercially available (3R,4R,5R)-5-(2,4-dichloro-benzyloxymethyl)-4-(2,4-dichloro-benzyloxy)-2-methoxy-tetrahydrofuran-3-acetate I-1 and 4-chloro-5-iodo-pyrrolo[2,3-d]pyrimidine according to General Procedure 1.

Alternatively, the compound is prepared according to General Procedure 2a and General Procedure 3.

White solid. $^1$H-NMR (300 MHz, DMSO-d$_6$): δ 8.10 (1H, s), 7.75 (1H, s), 6.62 (2H, bs), 6.20 (2H, d, J=2.38 Hz), 5.60 (1H, d, J=7.38 Hz), 5.18 (1H, t, J=5.18 Hz), 4.31 (dd, J=8.64, 7.47 Hz, 1H), 3.84-3.76 (2H, m), 3.65-3.64 (1H, m), 3.07 (1H, s). ESI-MS: calcd. for C$_{13}$H$_{13}$IN$_4$O$_4$ (416.2). found: 417.2 (M+1).

$^{13}$C NMR (75 MHz, DMSO-d$_6$): δ 157.80, 150.71, 144.96, 127.45, 103.48, 90.16, 82.63, 82.49, 77.31, 76.50, 74.18, 59.85, 52.29.

Example 8

(2R,3R,4R,5R)-2-(4-Amino-5-ethynyl-pyrrolo[2,3-d]pyrimidin-7-yl)-3-ethynyl-5-hydroxymethyl-tetrahydro-furan-3,4-diol

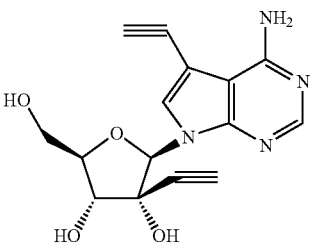

The title compound is prepared from commercially available (3R,4R,5R)-5-(2,4-dichlorobenzyloxymethyl)-4-(2,4-dichloro-benzyloxy)-2-methoxy-tetrahydrofuran-3-acetate I-1 and 4-chloro-5-acetylene-pyrrolo[2,3-d]pyrimidine or 4-chloro-5-trimethylsilylethynyl-7H-pyrrolo[2,3-d]pyrimidine according to General Procedure 2a and General Procedure 3.

Alternatively, the title compound and the compounds of Examples 9 and 10 are prepared from (2R,3R,4R,5R)-2-(4-amino-5-iodo-pyrrolo[2,3-d]pyrimidin-7-yl)-3-ethynyl-5-hydroxymethyl-tetrahydrofuran-3,4-diol (Example 7). To a dried and precooled 25 ml round-bottomed flask are added (2R,3R,4R,5R)-2-(4-amino-5-iodo-pyrrolo[2,3-d]pyrimidin-7-yl)-3-ethynyl-5-hydroxymethyl-tetrahydrofuran-3,4-diol (0.060 g, 0.144 mmol), copper(I) iodide (0.006 g, 0.028 mmol), tetrakis(triphenylphosphine)palladium(0) (0.016 g, 0.014 mmol) dissolved in anhydrous THF (1.0 ml) and anhydrous DMF (0.5 ml), triethylamine (0.04 ml, 0.288 mmol), trimethylsilylacetylene (0.024 ml, 0.173 mmol). The reaction mixture is stirred at 0° C. to room temperature under argon for 30 mins. The solvent is removed in vacuo, and the residue obtained is dissolved in methanol (0.60 ml) and 30% ammonia solution (0.60 ml). The resulting reaction mixture is allowed to stir at room temperature for one hour. The solvent is removed in vacuo. The crude residue obtained is purified by reverse phase preparative HPLC on Atlantis C$^{18}$ column (250×20 mm) in gradient from 5 to 95% of acetonitrile in water. Fractions containing the desired products are isolated, evaporated and lyophilized from water to give (2R,3R,4R,5R)-2-(4-amino-5-ethynyl-pyrrolo[2,3-d]pyrimidin-7-yl)-3-ethynyl-5-hydroxymethyl-tetrahydro-furan-3,4-diol (Example 8), (2R,3R,4R,5R)-2-(4-amino-5-ethynyl-pyrrolo[2,3-d]pyrimidin-7-yl)-3-buta-1,3-diynyl-5-hydroxymethyl-tetrahydro-furan-3,4-diol (Example 9), and (2R,3R,4R,5R)-2-(4-amino-5-iodo-pyrrolo[2,3-d]pyrimidin-7-yl)-3-buta-1,3-diynyl-5-hydroxymethyl-tetrahydro-furan-3,4-diol (Example 10) as white solid.

White solid. $^1$H-NMR (300 MHz, DMSO-$d_6$): δ 8.14 (1H, s), 7.88 (1H, s), 6.62 (1H, bs), 6.26-6.20 (2H, m), 5.70 (1H, bs), 5.25 (1H, bs), 4.33 (d, J=8.79 Hz, 1H), 4.26 (1H, s), 3.85-3.62 (4H, m), 3.06 (1H, s).

ESI-MS: calcd. for $C_{15}H_{14}IN_4O_4$ (314.3). found: 315.3 (M+1).

Example 9

(2R,3R,4R,5R)-2-(4-Amino-5-ethynyl-pyrrolo[2,3-d]pyrimidin-7-yl)-3-buta-1,3-diynyl-5-hydroxymethyl-tetrahydro-furan-3,4-diol

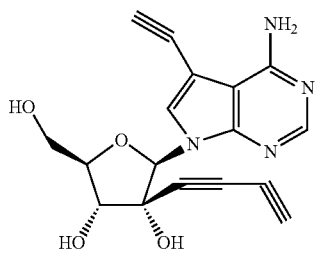

The title compound is prepared as described above for Example 8.

White solid. $^1$H-NMR (300 MHz, DMSO-$d_6$): δ 8.15 (1H, s), 7.92 (1H, s), 6.60 (2H, bs), 6.21 (1H, s), 5.80 (1H, bs), 5.25 (1H, bs), 4.36 (d, J=9.08 Hz, 1H), 4.28 (1H, s), 3.88-3.78 (2H, m), 3.67-3.62 (2H, m), 3.54 (1H, s).

ESI-MS: calcd. for $C_{17}H_{14}N_4O_4$ (338.3). found: 339.3 (M+1).

Example 10

(2R,3R,4R,5R)-2-(4-Amino-5-iodo-pyrrolo[2,3-d]pyrimidin-7-yl)-3-buta-1,3-diynyl-5-hydroxymethyl-tetrahydro-furan-3,4-diol

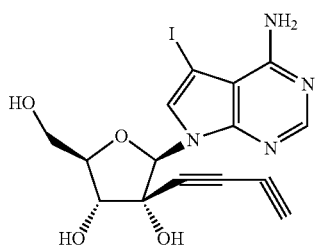

The title compound is prepared as described above for Example 8.

White solid. ESI-MS: calcd. for $C_{15}H_{13}IN_4O_4$ (440.2). found: 441.2 (M+1).

Example 11

Synthesis of Base Moieties

4-Chloro-7H-pyrrolo[2,3-d]pyrimidine is commercially available. 4-Chloro-5-fluoro-pyrrolo[2,3-d]pyrimidine may be synthesized as described in X Wang, P P Seth, R Ranken, E E Swayze and M T Migawa, Nucleosides, Nucleotides and Nucleic Acids, 23:1, 161-170. 7H-Pyrrolo[2,3-d]pyrimidin-4-yl-isoindole-1,3-dione may be synthesized as described in M M Bio, F Xu, M Waters, J M Willimas, K A Savery, C J Cowden, C Yang, E Buck, Z J Song, D M Tschaen, R P Volante, R A Reamer, E J J Grabowski, J. Org. Chem. 2004, 69, 6257-6266. 4-Chloro-5-iodo-pyrrolo[2,3-d]pyrimidine and 4-chloro-5-acetylene-pyrrolo[2,3-d]pyrimidine may be synthesized from 4-chloro-7H-pyrrolo[2,3-d]pyrimidine as described below. Where the base 7H-pyrrolo[2,3-d]pyrimidin-4-yl-isoindole-1,3-dione is coupled to the sugar moiety as described in General Procedure 3, the protecting group may be removed after the coupling step, under basic conditions such as 1-butylamine in methanol (e.g. with heating at 65° C. for 12 h). The corresponding 4-amino-pyrrolo[2,3-d]pyrimidin-7-yl nucleoside may thereby be obtained.

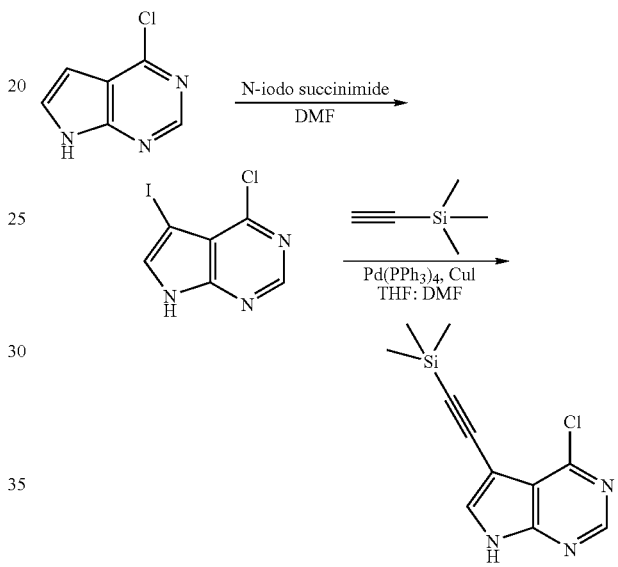

Example 11.1

To a 250 ml round-bottomed flask, protected from light with aluminum foil, are added 4-chloro-7H-pyrrolo[2,3-d]pyrimidine 1 (2.15 g, 14.0 mmol) and N-iodosuccinimide (3.37 g, 14.98 mmol) dissolved in anhydrous DMF. The reaction mixture is stirred at room temperature under nitrogen for 16 hrs. The solvent is removed in vacuo, and the residue is dissolved in methylene chloride (250 ml). The reaction mixture is washed with brine (50 ml), and the organic layer is separated, dried over $Na_2SO_4$, and concentrated in vacuo. The crude residue is purified by flash-chromatography on silica gel and eluted with 60% EtOAc in cyclohexane. Fractions containing the desired product (TLC) are pooled and evaporated to afford 4-chloro-5-iodo-pyrrolo[2,3-d]pyrimidine as a pale-yellow solid.

ESI-MS: calcd. for $C_6H_3ClIN_3$ (279.4). found: 280.07 (M+1).

Example 11.2

To a 250 ml round-bottomed flask, protected from light with aluminum foil, are added 4-chloro-5-iodo-7H-pyrrolo[2,3-d]pyrimidine (1.3 g, 4.6 mmol), copper(I) iodide (0.17 g, 0.93 mmol), trimethylsilylacetylene (0.96 ml, 6.97 mmol), and tetrakis(triphenylphosphine)palladium(0) (0.26 g, 0.23 mmol) dissolved in anhydrous THF (60 ml), anhydrous DMF (20 ml) and triethyl amine (0.64 ml, 4.65 mmol). The reaction mixture is stirred at room temperature under nitrogen for 16 hrs. The solvent is removed in vacuo, and the residue is dissolved in methylene chloride (250 ml). The reaction mixture is washed with water (3×50 ml), and the combined organic layer is dried over $Na_2SO_4$, and concentrated in vacuo. The crude residue is purified by flash-chromatography on silica gel and eluted with 70% EtOAc in cyclohexane. Fractions containing the desired product (TLC) are pooled and evaporated to afford 4-chloro-5-trimethylsilylethynyl-7H-pyrrolo[2,3-d]pyrimidine as a tan white solid.

$^1$H-NMR (300 MHz, DMSO-$d_6$): δ 12.92 (1H, s), 8.62 (1H, s), 8.06 (1H, s), 0.23 (9H, s).

ESI-MS: calcd. for $C_{11}H_{12}ClN_3Si$ (249.7). found: 250.2 (M+1).

4-Chloro-5-trimethylsilylethynyl-7H-pyrrolo[2,3-d]pyrimidine may either be used directly in the coupling step, as shown in General Procedure 3, in which case the trimethylsilyl group is cleaved under the coupling reaction conditions, or it may be converted to 4-chloro-5-acetylene-pyrrolo[2,3-d]pyrimidine by desilylation using, e.g., ammonia, NaOH or KOH.

II. Antiviral Activity of Compounds of the Invention

The compounds of the invention are active against various members of the Flaviviridae family. The activities of the compounds of the invention may be shown in standard in vitro and in vivo tests.

50% effective concentration ($EC_{50}$), is the concentration of the test compound that decreases the signal generated by the virus by 50%. It is calculated using nonlinear regression analysis using the variable slope sigmoidal dose-response curve, with commercial software such as Prism or Activity-Base.

Example 12

Cell-Based Flavivirus Immunodetection (CFI) Assay

BHK21 or A549 cells are trypsinized, counted and diluted to $2×10^5$ cells/ml in Hams F-12 media (for A549 cells) or RPMI-1640 media (for BHK21 cells) supplemented with 2% fetal bovine serum and 1% penicillin/streptomycin. $2×10^4$ cells are dispensed in clear 96-well tissue culture plate per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ in the same media. The media containing viruses and the compounds are removed, replaced with fresh medium containing only the test compounds and incubated at 37° C., 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 μl of 3,3',5,5'-tetramethylbenzidine (TMB) substrate solution (Sigma) is added to each well for two minutes. The reaction is stopped by addition 0.5M sulfuric acid. The plates are read at 450 nm absorbance for viral load quantification. After measurement, the cells are washed three times with PBS, followed by incubation with propidium iodide for 5 min. The plate is read in a Tecan Safire plate reader (excitation 537 nm, emission 617 nm) for cell number quantification. Dose response curves are plotted from the mean absorbance versus the log of the concentration of test compounds. The $EC_{50}$ is calculated by nonlinear regression analysis. A positive control may be used, such as, for example, N-nonyl-deoxynojirimycin.

Example 13

Cell-Based Flavivirus Cytopathic Effect (CPE) Assay

For testing against West Nile virus or Japanese encephalitis virus, BHK21 cells are trypsinized and diluted to a concentration of $4×10^5$ cells/ml in RPMI-1640 media supplemented with 2% fetal bovine serum and 1% penicillin/streptomycin. For testing against dengue virus, Huh7 cells are trypsinized and diluted to a concentration of $4×10^5$ cells/ml in DMEM media supplemented with 5% fetal bovine serum and 1% penicillin/streptomycin. A 50 μl of cell suspension ($2×10^4$ cells) is dispensed per well in the 96-well optical bottom PIT polymerbase plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hrs. At the end of incubation, 100 μl of CellTiter-Glo® reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control may be used, such as, for example, N-nonyl-deoxynojirimycin.

Example 14

Cell-Based Hepatitis C Virus (HCV) Replicon Assay

HVC replicon-containing cells, Huh-luc/neo-ET, are maintained in DMEM medium containing 2 mM L-glutamate, 0.1 mM non-essential amino acid solution, 10% heat-inactivated fetal bovine serum and 250 mg/ml Geneticin®, G418 sulfate solution. The cells are kept between 20 to 80% confluency and are trypsinized with trypsin (0.05%)/EDTA solution. After trypsinization, cells are resuspended in supplemented DMEM phenol red-free medium (DMEM phenol red free supplemented with 2 mM L-glutamine, 0.1 mM non-essential amino acid solution, 10% of heat-inactivated fetal bovine serum and 1 mM sodium pyruvate) and pelleted by centrifugation at 420 g for 5 min. Cell density is calculated and diluted to $1×10^5$ cells/mL with phenol red-free medium. Two sets of plates are prepared, a white opaque 96-well plate for the luciferase reading and a 96-well clear plate for cytotoxicity measurement. Each well is seeded with 10,000 cells/well and incubated overnight at 37° C., 5% $CO_2$. After incubation, the medium is aspirated and phenol red free medium supplemented with various concentrations of compounds is added and the plates further incubated for at 37° C., 5% $CO_2$ for another 48 hours. As a positive control may be used, for example, NM107 (2'-C-methylcytidine).

For determination of luciferase activity, the plates are removed from the incubator to allow them to equilibrate to room temperature for 30 minutes and luciferase activity is measured after the addition of 100 µL of the Britelite® (Per-Kin Elmer) prepared according to manufacturer's instructions.

III. Antiviral Activities of the Compounds of the Invention in a Mouse Model of Dengue Infection

Example 15

The compounds of the invention also show activity in vivo in a mouse model of dengue infection (Schul et al. Journal of Infectious Diseases 2007; 195:665-74). Briefly, AG129 mice (B&K Universal Ltd, Hull, UK) are housed in individually ventilated cages (TechniPlast, Italy) and used between 6 and 10 weeks of age. Mice are injected intraperitoneally with 0.4 ml TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. 20 µl of plasma is diluted in 780 µl RPMI 1640 medium and snap frozen in liquid nitrogen for plaque assay analysis. Remaining plasma is used for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water); or 6N HCl (1.5 eq):1N NaOH (pH adjusted to 3.5):100 mM citrate buffer pH 3.5 (0.9% v/v: 2.5% v/v: 96.6% v/v). Thirty six 6-10 week old AG129 mice are divided into six groups of six mice each. All mice are infected with dengue virus as described above (day 0). Group 1 is dosed by oral gavage of 200 ml/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of a compound of the invention respectively. A positive control may be used, such as, e.g., an antiviral compound or (2R,3R,4R,5R)-2-(2-amino-6-hydroxy-purin-9-yl)-5-hydroxymethyl-3-methyl-tetrahydro-furan-3,4-diol, dosed by oral gavage of 200 µl/mouse the same way as the previous groups. A further group is treated with only vehicle fluid.

On day 3 post-infection approximately 100 µl blood samples, anti-coagulated with sodium citrate, are taken from the mice by retro-orbital puncture under isoflurane anaesthesia. Plasma is obtained from each blood sample by centrifugation and snap frozen in liquid nitrogen for plaque assay analysis. The collected plasma samples are analyzed by plaque assay as described in Schul et al. Journal of Infectious Diseases 2007; 195:665-74. Cytokines are also analysed as described in Schul et al. Journal of Infectious Diseases 2007; 195:665-74. NS1 protein levels are analysed using a Platelia® kit (BioRad Laboratories). An anti-viral effect is indicated by a reduction in cytokine levels and/or NS1 protein levels.

The compounds of the invention demonstrate dose response inhibition with dosages of 5-50 mg/kg bid giving a reduction in viremia of about 5-100 fold, for example about 10-60 fold, for example about 20-30 fold, compared to the control group. For example, the compound of Example 1 demonstrates dose response inhibition with a dosage of 25 mg/kg bid giving a reduction in viremia of about 20-fold.

IV. Clinical Trial Protocol for a Dengue Clinical Trial

Clinical trials may be conducted, for example in the following way. A Phase I study is a randomized, placebo-controlled dose escalation trial in 64 healthy adult volunteers to assess safety, tolerability and pharmacokinetics following single and multiple oral doses. Seven days of dosing is performed on the basis that a dengue viremia typically lasts 5-7 days. The effect of food on plasma drug levels is assessed in one cohort of volunteers.

A Phase IIa study is a randomized, placebo-controlled dose escalation trial to evaluate antiviral activity of a compound of the invention in adult patients with acute dengue. There are three cohorts, with a total of about 60 subjects. Eligible hospital inpatients are randomised to drug or placebo within 48 hrs of illness onset to provide the greatest opportunity to observe a antiviral or clinical effect. Dosing occurs daily or as indicated by the pharmacokinetic properties of the drug for up to 3 days. Clinical, hematological, biochemical and virological markers are measured four times daily until 72 hrs after defervescence. The primary laboratory endpoint is time to resolution of viremia. The primary clinical endpoint is time to resolution of fever. A significant reduction in time to resolution of viremia is a demonstration of success. Secondary measures may include time to resolution of NS1 antigenemia, time to restoration of thrombocytopenia and requirement for any intravenous fluid replacement.

It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A compound of formula (I), or a pharmaceutically acceptable salt or prodrug thereof:

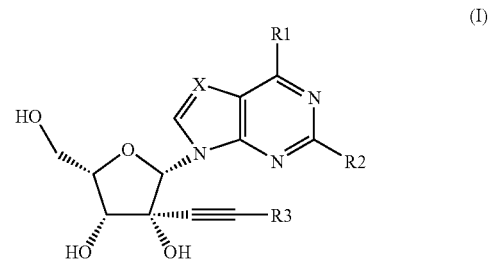

wherein:
 X is CH or CR4;
 R1 is halogen, NR5R6 or OR7;
 R2 is H, halogen, or NR5R6;
 R3 is H, alkyl, alkenyl, alkynyl, aryl, cycloalkyl, heterocycloalkyl or heteroaryl, each of which is optionally substituted with one or more substituents;
 R4 is alkyl, alkenyl, alkynyl, aryl, cycloalkyl, heterocycloalkyl, heteroaryl, halogen, cyano, nitro, hydroxy, alkoxy, alkylthio, amino, alkylamino, carboxy, carboxamide or alkyloxycarbonyl, each of which is optionally substituted with one or more substituents;
 R5 and R6 are independently selected from the group consisting of H, alkyl, alkenyl, alkynyl, aryl, cycloalkyl, heterocycloalkyl, heteroaryl, amino, alkylamino, arylamino, hydroxy, alkoxy, arylcarbonyl and alkylcarbonyl, each of which is optionally substituted with one or more substituents; and
 R7 is H, alkyl, alkenyl, alkynyl, aryl, cycloalkyl, heterocycloalkyl, heteroaryl, alkylcarbonyl or arylcarbonyl, each of which is optionally substituted with one or more substituents.

2. The compound as claimed in claim 1 which is a compound of formula (II), or a pharmaceutically acceptable salt or prodrug thereof:

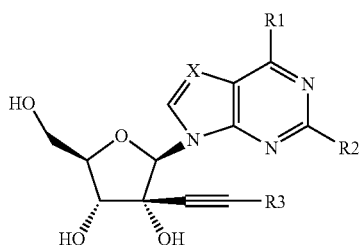

(II)

wherein:

X is CH or CR4;

R1 is halogen, NR5R6 or OR7;

R2 is H, halogen, or NR5R6;

R3 is H, alkyl, alkenyl, alkynyl, aryl, cycloalkyl, heterocycloalkyl or heteroaryl, each of which is optionally substituted with one or more substituents;

R4 is alkyl, alkenyl, alkynyl, aryl, cycloalkyl, heterocycloalkyl, heteroaryl, halogen, cyano, nitro, hydroxy, alkoxy, alkylthio, amino, alkylamino, carboxy, carboxamide or alkyloxycarbonyl, each of which is optionally substituted with one or more substituents;

R5 and R6 are independently selected from the group consisting of H, alkyl, alkenyl, alkynyl, aryl, cycloalkyl, heterocycloalkyl, heteroaryl, amino, alkylamino, arylamino, hydroxy, alkoxy, arylcarbonyl and alkylcarbonyl, each of which is optionally substituted with one or more substituents; and R7 is H, alkyl, alkenyl, alkynyl, aryl, cycloalkyl, heterocycloalkyl, heteroaryl, alkylcarbonyl or arylcarbonyl, each of which is optionally substituted with one or more substituents.

3. A compound selected from the group consisting of:

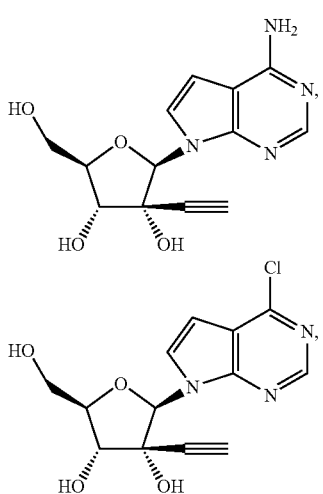

-continued

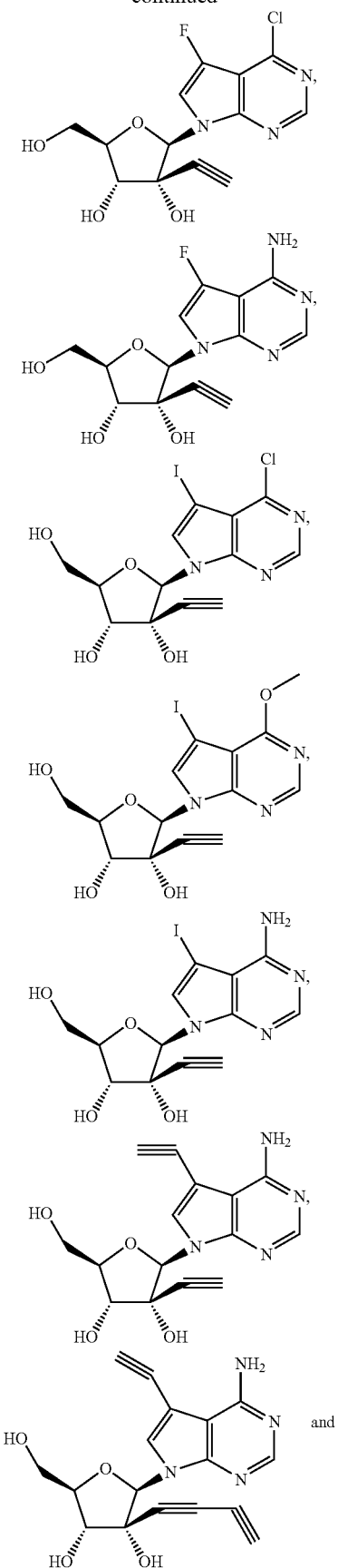

and

-continued

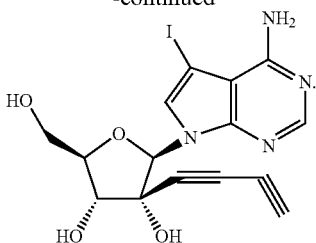

4. (2R,3R,4R,5R)-2-(4-amino-pyrrolo[2,3-d]pyrimidin-7-yl)-3-ethynyl-5-hydroxymethyl-tetrahydrofuran-3,4-diol.

5. (2R,3R,4R,5R)-2-(4-amino-5-ethynyl-pyrrolo[2,3-d]pyrimidin-7-yl)-3-ethynyl-5-hydroxymethyl-tetrahydrofuran-3,4-diol or (2R,3R,4R,5R)-2-(4-amino-5-fluoro-pyrrolo[2,3-d]pyrimidin-7-yl)-3-ethynyl-5-hydroxymethyl-tetrahydrofuran-3,4-diol.

6. A pharmaceutical composition comprising a compound as claimed in claim 1, or a pharmaceutically acceptable salt or prodrug thereof, in combination with a pharmaceutically acceptable excipient, diluent or carrier.

7. A method of treating a disease caused by infection by a virus selected from the group consisting of dengue virus, yellow fever virus, West Nile virus, Japanese encephalitis virus, tick-borne encephalitis, Kuhjin virus, Murray Valley encephalitis virus, St. Louis encephalitis virus, Omsk hemorrhagic fever virus, bovine viral diarrhea virus, Zika virus, and hepatitis C virus, comprising administering to a patient in need thereof an effective amount of a compound of claim 1.

8. The method of claim 7 wherein the viral infection is caused by dengue virus.

* * * * *